(12) United States Patent
Qu et al.

(10) Patent No.: US 10,793,643 B2
(45) Date of Patent: Oct. 6, 2020

(54) PCSK9 ANTIBODY, ANTIGEN-BINDING FRAGMENT THEREOF, AND MEDICAL APPLICATION THEREOF

(71) Applicants: Jiangsu Hengrui Medicine Co., Ltd., Lianyungang, Jiangsu (CN); Shanghai Hengrui Pharmaceutical Co., Ltd., Shanghai (CN)

(72) Inventors: Xiangdong Qu, Shanghai (CN); Xin Ye, Shanghai (CN); Shaoyu Xu, Shanghai (CN); Bei Yuan, Shanghai (CN); Dongbing Cui, Shanghai (CN); Qiyue Hu, Shanghai (CN); Lei Zhang, Shanghai (CN); Zhibin Xu, Shanghai (CN); Weikang Tao, Shanghai (CN); Lianshan Zhang, Shanghai (CN); Piaoyang Sun, Jiangsu (CN)

(73) Assignees: Jiangsu Hengrui Medicine Co., Ltd., Lianyungang, Jiangsu (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 241 days.

(21) Appl. No.: 16/066,567

(22) PCT Filed: Dec. 20, 2016

(86) PCT No.: PCT/CN2016/111053
§ 371 (c)(1),
(2) Date: Jun. 27, 2018

(87) PCT Pub. No.: WO2017/114230
PCT Pub. Date: Jul. 6, 2017

(65) Prior Publication Data
US 2019/0016825 A1 Jan. 17, 2019

(30) Foreign Application Priority Data
Dec. 31, 2015 (CN) .......................... 2015 1 1024618

(51) Int. Cl.
| | | |
|---|---|---|
| *C07K 16/40* | (2006.01) | |
| *C12N 9/64* | (2006.01) | |
| *A61K 39/395* | (2006.01) | |
| *A61P 3/06* | (2006.01) | |
| *C12N 15/62* | (2006.01) | |
| *A61K 39/00* | (2006.01) | |

(52) U.S. Cl.
CPC ............ *C07K 16/40* (2013.01); *A61K 39/395* (2013.01); *A61K 39/3955* (2013.01); *A61P 3/06* (2018.01); *C12N 9/64* (2013.01); *C12N 15/62* (2013.01); *A61K 2039/505* (2013.01); *C07K 2317/24* (2013.01); *C07K 2317/51* (2013.01); *C07K 2317/515* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,165,745 | A | 12/2000 | Ward et al. |
| 6,277,375 | B1 | 8/2001 | Ward |
| 7,083,784 | B2 | 8/2006 | Dall'Acqua et al. |
| 7,658,921 | B2 | 2/2010 | Dall'Acqua et al. |
| 8,563,698 | B2 | 10/2013 | Jackson et al. |
| 8,829,165 | B2 | 9/2014 | Jackson et al. |
| 8,859,741 | B2 | 10/2014 | Jackson et al. |
| 8,871,913 | B2 | 10/2014 | Jackson et al. |
| 8,871,914 | B2 | 10/2014 | Jackson et al. |
| 8,883,983 | B2 | 11/2014 | Jackson et al. |

FOREIGN PATENT DOCUMENTS

| | | |
|---|---|---|
| CN | 101939338 A | 1/2011 |
| CN | 102245641 A | 11/2011 |
| CN | 102333542 A | 1/2012 |
| CN | 103261230 A | 8/2013 |
| CN | 103781802 A | 5/2014 |
| CN | 104861071 A | 8/2015 |
| CN | 105001336 A | 10/2015 |
| WO | 02/060919 A2 | 8/2002 |
| WO | 2011072263 A1 | 6/2011 |
| WO | 2011111007 A2 | 9/2011 |
| WO | 2012054438 A1 | 4/2012 |

(Continued)

OTHER PUBLICATIONS

MacCallum et al. "Antibody-antigen interactions: contact analysis and binding site topography", J. Mol. Biol. vol. 262, pp. 732-745, 1996.*
De Pascalis et al. "Grafting of abbreviated complementarity determining regions containing specificity determining residues essential for ligand contact to engineer a less immunogenic humanzied monoclonal antibody", J. Immunol. 169, pp. 3076-3084, 2002.*
Dall'Acqua et al., "Properties of Human IgG1s Engineered for Enhanced Binding to the Neonatal Fc Receptor (FcRn)" The Journal of Biological Chemistry, vol. 281, No. 33, pp. 23514-23524, 2006.
Stein et al. "Effect of Monoclonal Antibody to PCSK9 on LDL Cholesterol" The New England Journal of Medicine, 366; 12, pp. 1108-1118, Mar. 2012.

(Continued)

*Primary Examiner* — Nora M Rooney
(74) *Attorney, Agent, or Firm* — Ice Miller LLP

(57) ABSTRACT

The present invention provides a PCSK9 antibody, an antigen-binding fragment thereof, and a medicinal application thereof. Provided in the invention is a chimeric antibody and a humanized antibody, both comprising a CDR of the PCSK9 antibody, and a pharmaceutical composition comprising the PCSK9 antibody and an antigen-binding fragment thereof, and an application of the PCSK9 antibody as a lipid-lowering agent. The invention specifically relates to an application of a humanized PCSK9 antibody for preparing a pharmaceutical drug to treat a PCSK9-induced disease or symptom.

24 Claims, 4 Drawing Sheets
Specification includes a Sequence Listing.

(56) References Cited

FOREIGN PATENT DOCUMENTS

| WO | 2012058137 | A2 | 5/2012 |
|---|---|---|---|
| WO | 2012088313 | A1 | 6/2012 |
| WO | 2012101251 | A1 | 8/2012 |
| WO | 2012109530 | A1 | 8/2012 |
| WO | 2012154999 | A1 | 11/2012 |
| WO | 2012168491 | A1 | 12/2012 |
| WO | 2012170607 | A2 | 12/2012 |
| WO | 2013008185 | A1 | 1/2013 |
| WO | 2013016648 | A2 | 1/2013 |
| WO | 2013039958 | A1 | 3/2013 |
| WO | 2013039969 | A1 | 3/2013 |
| WO | 2013091103 | A1 | 6/2013 |
| WO | 2013148284 | A1 | 10/2013 |
| WO | 2013169886 | A1 | 11/2013 |
| WO | 2013170367 | A1 | 11/2013 |
| WO | 2013188855 | A1 | 12/2013 |

OTHER PUBLICATIONS

Zhang, L.W. et al., "An Anti-PCSK9 Antibody Reduces LDL-Cholesterol on Top of a Statin and Suppresses Hepatocyte SREBP-Regulated Genes", Int. J. Biol. Sci., vol. 8, No. 3, 09 , pp. 310-327, Feb. 2012.

\* cited by examiner

SEQUENCE LISTING

<160> NUMBER OF SEQ ID NOS: 33

<210> SEQ ID NO 1
<211> LENGTH: 698
<212> TYPE: PRT
<213> ORGANISM: Artificial
<220> FEATURE:
<223> OTHER INFORMATION: PCSK9 with his tag:PCSK9-His6, used as
      immunogen for immunizing mice or as a detection reagent

<400> SEQUENCE: 1

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Arg Ser Glu
            35                  40                  45

Glu Asp Gly Leu Ala Glu Ala Pro Glu His Gly Thr Thr Ala Thr Phe
        50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
            355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
        675                 680                 685

Gln Glu Leu Gln His His His His His
690                 695

<210> SEQ ID NO 2
<211> LENGTH: 714
<212> TYPE: PRT
<213> ORGANISM: ARTIFICIAL
<220> FEATURE:
<223> OTHER INFORMATION: PCSK9 with PADRE peptide and His tag: PCSK9-
      PADRE-His6, as an immunogen, contained PADRE peptide can promote
      immunization

<400> SEQUENCE: 2

Met Gly Thr Val Ser Ser Arg Arg Ser Trp Trp Pro Leu Pro Leu Leu

-continued

```
1               5               10              15
Leu Leu Leu Leu Leu Leu Leu Gly Pro Ala Gly Ala Arg Ala Gln Glu
            20              25              30
Asp Glu Asp Gly Asp Tyr Glu Glu Leu Val Leu Ala Leu Arg Ser Glu
            35              40              45
Glu Asp Gly Leu Ala Glu Ala Pro Glu His Gly Thr Thr Ala Thr Phe
            50              55              60
His Arg Cys Ala Lys Asp Pro Trp Arg Leu Pro Gly Thr Tyr Val Val
65              70              75              80
Val Leu Lys Glu Glu Thr His Leu Ser Gln Ser Glu Arg Thr Ala Arg
            85              90              95
Arg Leu Gln Ala Gln Ala Ala Arg Arg Gly Tyr Leu Thr Lys Ile Leu
            100             105             110
His Val Phe His Gly Leu Leu Pro Gly Phe Leu Val Lys Met Ser Gly
            115             120             125
Asp Leu Leu Glu Leu Ala Leu Lys Leu Pro His Val Asp Tyr Ile Glu
            130             135             140
Glu Asp Ser Ser Val Phe Ala Gln Ser Ile Pro Trp Asn Leu Glu Arg
145             150             155             160
Ile Thr Pro Pro Arg Tyr Arg Ala Asp Glu Tyr Gln Pro Pro Asp Gly
            165             170             175
Gly Ser Leu Val Glu Val Tyr Leu Leu Asp Thr Ser Ile Gln Ser Asp
            180             185             190
His Arg Glu Ile Glu Gly Arg Val Met Val Thr Asp Phe Glu Asn Val
            195             200             205
Pro Glu Glu Asp Gly Thr Arg Phe His Arg Gln Ala Ser Lys Cys Asp
            210             215             220
Ser His Gly Thr His Leu Ala Gly Val Val Ser Gly Arg Asp Ala Gly
225             230             235             240
Val Ala Lys Gly Ala Ser Met Arg Ser Leu Arg Val Leu Asn Cys Gln
            245             250             255
Gly Lys Gly Thr Val Ser Gly Thr Leu Ile Gly Leu Glu Phe Ile Arg
            260             265             270
Lys Ser Gln Leu Val Gln Pro Val Gly Pro Leu Val Val Leu Leu Pro
            275             280             285
Leu Ala Gly Gly Tyr Ser Arg Val Leu Asn Ala Ala Cys Gln Arg Leu
            290             295             300
Ala Arg Ala Gly Val Val Leu Val Thr Ala Ala Gly Asn Phe Arg Asp
305             310             315             320
Asp Ala Cys Leu Tyr Ser Pro Ala Ser Ala Pro Glu Val Ile Thr Val
            325             330             335
Gly Ala Thr Asn Ala Gln Asp Gln Pro Val Thr Leu Gly Thr Leu Gly
            340             345             350
Thr Asn Phe Gly Arg Cys Val Asp Leu Phe Ala Pro Gly Glu Asp Ile
            355             360             365
Ile Gly Ala Ser Ser Asp Cys Ser Thr Cys Phe Val Ser Gln Ser Gly
            370             375             380
Thr Ser Gln Ala Ala Ala His Val Ala Gly Ile Ala Ala Met Met Leu
385             390             395             400
Ser Ala Glu Pro Glu Leu Thr Leu Ala Glu Leu Arg Gln Arg Leu Ile
            405             410             415
His Phe Ser Ala Lys Asp Val Ile Asn Glu Ala Trp Phe Pro Glu Asp
            420             425             430
```

```
Gln Arg Val Leu Thr Pro Asn Leu Val Ala Ala Leu Pro Pro Ser Thr
            435                 440                 445

His Gly Ala Gly Trp Gln Leu Phe Cys Arg Thr Val Trp Ser Ala His
        450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
                500                 505                 510

Asn Ala Phe Gly Gly Glu Gly Val Tyr Ala Ile Ala Arg Cys Cys Leu
            515                 520                 525

Leu Pro Gln Ala Asn Cys Ser Val His Thr Ala Pro Pro Ala Glu Ala
        530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
                580                 585                 590

Glu Ala Ser Ile His Ala Ser Cys Cys His Ala Pro Gly Leu Glu Cys
            595                 600                 605

Lys Val Lys Glu His Gly Ile Pro Ala Pro Gln Glu Gln Val Thr Val
        610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
                660                 665                 670

Thr Ala Val Ala Ile Cys Cys Arg Ser Arg His Leu Ala Gln Ala Ser
            675                 680                 685

Gln Glu Leu Gln Gly Ser Gly Ala Lys Phe Val Ala Ala Trp Thr Leu
        690                 695                 700

Lys Ala Ala Ala His His His His His
705                 710

<210> SEQ ID NO 3
<211> LENGTH: 704
<212> TYPE: PRT
<213> ORGANISM: ARTIFICIAL
<220> FEATURE:
<223> OTHER INFORMATION: Fusion protein of PCSK9 containing TEV cleavage
      site and His tag: PCSK9-TEV-His6, N-PCSK9 (N terminal pCSK9
      domain) as an immunogen can be obtained via TEV enzyme digestion

<400> SEQUENCE: 3

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Arg Ser Glu
            35                  40                  45

Glu Asp Gly Leu Ala Glu Ala Pro Glu His Gly Thr Thr Ala Thr Phe
        50                  55                  60
```

```
His Arg Cys Ala Lys Asp Pro Trp Arg Leu Pro Gly Thr Tyr Val Val
 65                  70                  75                  80

Val Leu Lys Glu Glu Thr His Leu Ser Gln Ser Glu Arg Thr Ala Arg
                 85                  90                  95

Arg Leu Gln Ala Gln Ala Arg Arg Gly Tyr Leu Thr Lys Ile Leu
                100                 105                 110

His Val Phe His Gly Leu Leu Pro Gly Phe Leu Val Lys Met Ser Gly
                115                 120                 125

Asp Leu Leu Glu Leu Ala Leu Lys Leu Pro His Val Asp Tyr Ile Glu
                130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
                180                 185                 190

His Arg Glu Ile Glu Gly Arg Val Met Val Thr Asp Phe Glu Asn Val
                195                 200                 205

Pro Glu Glu Asp Gly Thr Arg Phe His Arg Gln Ala Ser Lys Cys Asp
                210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
                260                 265                 270

Lys Ser Gln Leu Val Gln Pro Val Gly Pro Leu Val Val Leu Leu Pro
                275                 280                 285

Leu Ala Gly Gly Tyr Ser Arg Val Leu Asn Ala Ala Cys Gln Arg Leu
                290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
                340                 345                 350

Thr Asn Phe Gly Arg Cys Val Asp Leu Phe Ala Pro Gly Glu Asp Ile
                355                 360                 365

Ile Gly Ala Ser Ser Asp Cys Ser Thr Cys Phe Val Ser Gln Ser Gly
                370                 375                 380

Thr Ser Gln Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
                420                 425                 430

Gln Arg Val Leu Thr Pro Asn Leu Val Ala Ala Leu Pro Pro Ser Thr
                435                 440                 445

His Glu Asn Leu Tyr Phe Gln Gly Ala Gly Trp Gln Leu Phe Cys Arg
                450                 455                 460

Thr Val Trp Ser Ala His Ser Gly Pro Thr Arg Met Ala Thr Ala Val
465                 470                 475                 480

Ala Arg Cys Ala Pro Asp Glu Glu Leu Leu Ser Cys Ser Ser Phe Ser
```

```
                485                 490                 495
Arg Ser Gly Lys Arg Gly Glu Arg Met Glu Ala Gln Gly Gly Lys
        500                 505                 510

Leu Val Cys Arg Ala His Asn Ala Phe Gly Gly Glu Gly Val Tyr Ala
        515                 520                 525

Ile Ala Arg Cys Cys Leu Leu Pro Gln Ala Asn Cys Ser Val His Thr
        530                 535                 540

Ala Pro Pro Ala Glu Ala Ser Met Gly Thr Arg Val His Cys His Gln
545                 550                 555                 560

Gln Gly His Val Leu Thr Gly Cys Ser Ser His Trp Glu Val Glu Asp
                565                 570                 575

Leu Gly Thr His Lys Pro Pro Val Leu Arg Pro Arg Gly Gln Pro Asn
            580                 585                 590

Gln Cys Val Gly His Arg Glu Ala Ser Ile His Ala Ser Cys Cys His
        595                 600                 605

Ala Pro Gly Leu Glu Cys Lys Val Lys Glu His Gly Ile Pro Ala Pro
610                 615                 620

Gln Glu Gln Val Thr Val Ala Cys Glu Glu Gly Trp Thr Leu Thr Gly
625                 630                 635                 640

Cys Ser Ala Leu Pro Gly Thr Ser His Val Leu Gly Ala Tyr Ala Val
                645                 650                 655

Asp Asn Thr Cys Val Val Arg Ser Arg Asp Val Ser Thr Thr Gly Ser
            660                 665                 670

Thr Ser Glu Gly Ala Val Thr Ala Val Ala Ile Cys Cys Arg Ser Arg
        675                 680                 685

His Leu Ala Gln Ala Ser Gln Glu Leu Gln His His His His His His
        690                 695                 700
```

<210> SEQ ID NO 4
<211> LENGTH: 698
<212> TYPE: PRT
<213> ORGANISM: ARTIFICIAL
<220> FEATURE:
<223> OTHER INFORMATION: PCSK9-D374Y mutant protein with His tag:
      PCSK9-D374Y-His6, as a detection reagent

<400> SEQUENCE: 4

```
Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Arg Ser Glu
            35                  40                  45

Glu Asp Gly Leu Ala Glu Ala Pro Glu His Gly Thr Thr Ala Thr Phe
        50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140
```

```
Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
            165                 170                 175

Gly Ser Leu Val Glu Val Tyr Leu Leu Asp Thr Ser Ile Gln Ser Asp
        180                 185                 190

His Arg Glu Ile Glu Gly Arg Val Met Val Thr Asp Phe Glu Asn Val
    195                 200                 205

Pro Glu Asp Gly Thr Arg Phe His Arg Gln Ala Ser Lys Cys Asp
210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
            245                 250                 255

Gly Lys Gly Thr Val Ser Gly Thr Leu Ile Gly Leu Glu Phe Ile Arg
        260                 265                 270

Lys Ser Gln Leu Val Gln Pro Val Gly Pro Leu Val Val Leu Leu Pro
    275                 280                 285

Leu Ala Gly Gly Tyr Ser Arg Val Leu Asn Ala Ala Cys Gln Arg Leu
290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
            325                 330                 335

Gly Ala Thr Asn Ala Gln Asp Gln Pro Val Thr Leu Gly Thr Leu Gly
        340                 345                 350

Thr Asn Phe Gly Arg Cys Val Asp Leu Phe Ala Pro Gly Glu Asp Ile
    355                 360                 365

Ile Gly Ala Ser Ser Tyr Cys Ser Thr Cys Phe Val Ser Gln Ser Gly
370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
            405                 410                 415

His Phe Ser Ala Lys Asp Val Ile Asn Glu Ala Trp Phe Pro Glu Asp
        420                 425                 430

Gln Arg Val Leu Thr Pro Asn Leu Val Ala Ala Leu Pro Pro Ser Thr
    435                 440                 445

His Gly Ala Gly Trp Gln Leu Phe Cys Arg Thr Val Trp Ser Ala His
450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
            485                 490                 495

Gly Glu Arg Met Glu Ala Gln Gly Gly Lys Leu Val Cys Arg Ala His
        500                 505                 510

Asn Ala Phe Gly Gly Glu Gly Val Tyr Ala Ile Ala Arg Cys Cys Leu
    515                 520                 525

Leu Pro Gln Ala Asn Cys Ser Val His Thr Ala Pro Ala Glu Ala
530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
```

```
                    565                 570                 575
Pro Val Leu Arg Pro Arg Gly Gln Pro Asn Gln Cys Val Gly His Arg
                580                 585                 590

Glu Ala Ser Ile His Ala Ser Cys Cys His Ala Pro Gly Leu Glu Cys
            595                 600                 605

Lys Val Lys Glu His Gly Ile Pro Ala Pro Gln Glu Gln Val Thr Val
        610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
        675                 680                 685

Gln Glu Leu Gln His His His His His His
    690                 695
```

<210> SEQ ID NO 5
<211> LENGTH: 719
<212> TYPE: PRT
<213> ORGANISM: ARTIFICIAL
<220> FEATURE:
<223> OTHER INFORMATION: PCSK9 protein inserted with biotin receiving peptide BP15 and His tag: PCSK9-BP15-His6. As a detection reagent, biotin will be labeled to BP15 peptide position during expression, avoiding the biotin labeling in vitro and consequently avoiding possible conformational changes.

<400> SEQUENCE: 5

```
Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205
```

```
Pro Glu Glu Asp Gly Thr Arg Phe His Arg Gln Ala Ser Lys Cys Asp
    210                 215                 220
Ser His Gly Thr His Leu Ala Gly Val Val Ser Gly Arg Asp Ala Gly
225                 230                 235                 240
Val Ala Lys Gly Ala Ser Met Arg Ser Leu Arg Val Leu Asn Cys Gln
                245                 250                 255
Gly Lys Gly Thr Val Ser Gly Thr Leu Ile Gly Leu Glu Phe Ile Arg
                260                 265                 270
Lys Ser Gln Leu Val Gln Pro Val Gly Pro Leu Val Leu Leu Pro
            275                 280                 285
Leu Ala Gly Gly Tyr Ser Arg Val Leu Asn Ala Ala Cys Gln Arg Leu
    290                 295                 300
Ala Arg Ala Gly Val Val Leu Val Thr Ala Ala Gly Asn Phe Arg Asp
305                 310                 315                 320
Asp Ala Cys Leu Tyr Ser Pro Ala Ser Ala Pro Glu Val Ile Thr Val
                325                 330                 335
Gly Ala Thr Asn Ala Gln Asp Gln Pro Val Thr Leu Gly Thr Leu Gly
                340                 345                 350
Thr Asn Phe Gly Arg Cys Val Asp Leu Phe Ala Pro Gly Glu Asp Ile
            355                 360                 365
Ile Gly Ala Ser Ser Asp Cys Ser Thr Cys Phe Val Ser Gln Ser Gly
    370                 375                 380
Thr Ser Gln Ala Ala Ala His Val Ala Gly Ile Ala Ala Met Met Leu
385                 390                 395                 400
Ser Ala Glu Pro Glu Leu Thr Leu Ala Glu Leu Arg Gln Arg Leu Ile
                405                 410                 415
His Phe Ser Ala Lys Asp Val Ile Asn Glu Ala Trp Phe Pro Glu Asp
                420                 425                 430
Gln Arg Val Leu Thr Pro Asn Leu Val Ala Ala Leu Pro Pro Ser Thr
            435                 440                 445
His Gly Ala Gly Trp Gln Leu Phe Cys Arg Thr Val Trp Ser Ala His
    450                 455                 460
Ser Gly Pro Thr Arg Met Ala Thr Ala Val Ala Arg Cys Ala Pro Asp
465                 470                 475                 480
Glu Glu Leu Leu Ser Cys Ser Ser Phe Ser Arg Ser Gly Lys Arg Arg
                485                 490                 495
Gly Glu Arg Met Glu Ala Gln Gly Gly Lys Leu Val Cys Arg Ala His
                500                 505                 510
Asn Ala Phe Gly Gly Glu Gly Val Tyr Ala Ile Ala Arg Cys Cys Leu
            515                 520                 525
Leu Pro Gln Ala Asn Cys Ser Val His Thr Ala Pro Pro Ala Glu Ala
    530                 535                 540
Ser Met Gly Thr Arg Val His Cys His Gln Gln Gly His Val Leu Thr
545                 550                 555                 560
Gly Cys Ser Ser His Trp Glu Val Glu Asp Leu Gly Thr His Lys Pro
                565                 570                 575
Pro Val Leu Arg Pro Arg Gly Gln Pro Asn Gln Cys Val Gly His Arg
                580                 585                 590
Glu Ala Ser Ile His Ala Ser Cys Cys His Ala Pro Gly Leu Glu Cys
            595                 600                 605
Lys Val Lys Glu His Gly Ile Pro Ala Pro Gln Glu Gln Val Thr Val
    610                 615                 620
Ala Cys Glu Glu Gly Trp Thr Leu Thr Gly Cys Ser Ala Leu Pro Gly
```

```
                625                 630                 635                 640

Thr Ser His Val Leu Gly Ala Tyr Ala Val Asp Asn Thr Cys Val Val
            645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
            675                 680                 685

Gln Glu Leu Gln Gly Ser Thr Ser Gly Ser Gly Leu Asn Asp Ile Phe
690                 695                 700

Glu Ala Gln Lys Ile Glu Trp His Glu His His His His His His
705                 710                 715

<210> SEQ ID NO 6
<211> LENGTH: 719
<212> TYPE: PRT
<213> ORGANISM: ARTIFICIAL
<220> FEATURE:
<223> OTHER INFORMATION: PCSK9 D374Y mutant protein inserted with biotin
      receiving peptide BP15 and His tag: PCSK9-D374Y-BP15-His6, as a
      detection protein

<400> SEQUENCE: 6

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
            35                  40                  45

Glu Asp Gly Leu Ala Glu Ala Pro Glu His Gly Thr Thr Ala Thr Phe
50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
            85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
            115                 120                 125

Asp Leu Leu Glu Leu Ala Leu Lys Leu Pro His Val Asp Tyr Ile Glu
            130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
            165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
            195                 200                 205

Pro Glu Glu Asp Gly Thr Arg Phe His Arg Gln Ala Ser Lys Cys Asp
210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
            245                 250                 255

Gly Lys Gly Thr Val Ser Gly Thr Leu Ile Gly Leu Glu Phe Ile Arg
            260                 265                 270
```

```
Lys Ser Gln Leu Val Gln Pro Val Gly Pro Leu Val Leu Leu Pro
        275                 280                 285

Leu Ala Gly Gly Tyr Ser Arg Val Leu Asn Ala Ala Cys Gln Arg Leu
290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Tyr Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
        675                 680                 685
```

```
Gln Glu Leu Gln Gly Ser Thr Ser Gly Ser Gly Leu Asn Asp Ile Phe
    690             695                 700
Glu Ala Gln Lys Ile Glu Trp His Glu His His His His His His
705                 710                 715
```

<210> SEQ ID NO 7
<211> LENGTH: 802
<212> TYPE: PRT
<213> ORGANISM: ARTIFICIAL
<220> FEATURE:
<223> OTHER INFORMATION: PCSK9 receptor protein LDLR extracellular
      domain with Flag tag and His tag: LDLR-ECD-Flag-His6 as a
      detection reagent

<400> SEQUENCE: 7

```
Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45

Ser Ala Glu Cys Gln Asp Gly Ser Asp Glu Ser Gln Glu Thr Cys Leu
50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Pro Lys Thr Cys Ser Gln Asp
            100                 105                 110

Glu Phe Arg Cys His Asp Gly Lys Cys Ile Ser Arg Gln Phe Val Cys
        115                 120                 125

Asp Ser Asp Arg Asp Cys Leu Asp Gly Ser Asp Glu Ala Ser Cys Pro
130                 135                 140

Val Leu Thr Cys Gly Pro Ala Ser Phe Gln Cys Asn Ser Ser Thr Cys
145                 150                 155                 160

Ile Pro Gln Leu Trp Ala Cys Asp Asn Asp Pro Asp Cys Glu Asp Gly
                165                 170                 175

Ser Asp Glu Trp Pro Gln Arg Cys Arg Gly Leu Tyr Val Phe Gln Gly
            180                 185                 190

Asp Ser Ser Pro Cys Ser Ala Phe Glu Phe His Cys Leu Ser Gly Glu
        195                 200                 205

Cys Ile His Ser Ser Trp Arg Cys Asp Gly Gly Pro Asp Cys Lys Asp
210                 215                 220

Lys Ser Asp Glu Glu Asn Cys Ala Val Ala Thr Cys Arg Pro Asp Glu
225                 230                 235                 240

Phe Gln Cys Ser Asp Gly Asn Cys Ile His Gly Ser Arg Gln Cys Asp
                245                 250                 255

Arg Glu Tyr Asp Cys Lys Asp Met Ser Asp Glu Val Gly Cys Val Asn
            260                 265                 270

Val Thr Leu Cys Glu Gly Pro Asn Lys Phe Lys Cys His Ser Gly Glu
        275                 280                 285

Cys Ile Thr Leu Asp Lys Val Cys Asn Met Ala Arg Asp Cys Arg Asp
290                 295                 300

Trp Ser Asp Glu Pro Ile Lys Glu Cys Gly Thr Asn Glu Cys Leu Asp
305                 310                 315                 320

Asn Asn Gly Gly Cys Ser His Val Cys Asn Asp Leu Lys Ile Gly Tyr
```

```
                325                 330                 335
Glu Cys Leu Cys Pro Asp Gly Phe Gln Leu Val Ala Gln Arg Arg Cys
            340                 345                 350
Glu Asp Ile Asp Glu Cys Gln Asp Pro Asp Thr Cys Ser Gln Leu Cys
            355                 360                 365
Val Asn Leu Glu Gly Gly Tyr Lys Cys Gln Cys Glu Glu Gly Phe Gln
            370                 375                 380
Leu Asp Pro His Thr Lys Ala Cys Lys Ala Val Gly Ser Ile Ala Tyr
385                 390                 395                 400
Leu Phe Phe Thr Asn Arg His Glu Val Arg Lys Met Thr Leu Asp Arg
            405                 410                 415
Ser Glu Tyr Thr Ser Leu Ile Pro Asn Leu Arg Asn Val Val Ala Leu
            420                 425                 430
Asp Thr Glu Val Ala Ser Asn Arg Ile Tyr Trp Ser Asp Leu Ser Gln
            435                 440                 445
Arg Met Ile Cys Ser Thr Gln Leu Asp Arg Ala His Gly Val Ser Ser
            450                 455                 460
Tyr Asp Thr Val Ile Ser Arg Asp Ile Gln Ala Pro Asp Gly Leu Ala
465                 470                 475                 480
Val Asp Trp Ile His Ser Asn Ile Tyr Trp Thr Asp Ser Val Leu Gly
            485                 490                 495
Thr Val Ser Val Ala Asp Thr Lys Gly Val Lys Arg Lys Thr Leu Phe
            500                 505                 510
Arg Glu Asn Gly Ser Lys Pro Arg Ala Ile Val Val Asp Pro Val His
            515                 520                 525
Gly Phe Met Tyr Trp Thr Asp Trp Gly Thr Pro Ala Lys Ile Lys Lys
            530                 535                 540
Gly Gly Leu Asn Gly Val Asp Ile Tyr Ser Leu Val Thr Glu Asn Ile
545                 550                 555                 560
Gln Trp Pro Asn Gly Ile Thr Leu Asp Leu Leu Ser Gly Arg Leu Tyr
            565                 570                 575
Trp Val Asp Ser Lys Leu His Ser Ile Ser Ser Ile Asp Val Asn Gly
            580                 585                 590
Gly Asn Arg Lys Thr Ile Leu Glu Asp Glu Lys Arg Leu Ala His Pro
            595                 600                 605
Phe Ser Leu Ala Val Phe Glu Asp Lys Val Phe Trp Thr Asp Ile Ile
            610                 615                 620
Asn Glu Ala Ile Phe Ser Ala Asn Arg Leu Thr Gly Ser Asp Val Asn
625                 630                 635                 640
Leu Leu Ala Glu Asn Leu Leu Ser Pro Glu Asp Met Val Leu Phe His
            645                 650                 655
Asn Leu Thr Gln Pro Arg Gly Val Asn Trp Cys Glu Arg Thr Thr Leu
            660                 665                 670
Ser Asn Gly Gly Cys Gln Tyr Leu Cys Leu Pro Ala Pro Gln Ile Asn
            675                 680                 685
Pro His Ser Pro Lys Phe Thr Cys Ala Cys Pro Asp Gly Met Leu Leu
            690                 695                 700
Ala Arg Asp Met Arg Ser Cys Leu Thr Glu Ala Glu Ala Ala Val Ala
705                 710                 715                 720
Thr Gln Glu Thr Ser Thr Val Arg Leu Lys Val Ser Ser Thr Ala Val
            725                 730                 735
Arg Thr Gln His Thr Thr Thr Arg Pro Val Pro Asp Thr Ser Arg Leu
            740                 745                 750
```

```
Pro Gly Ala Thr Pro Gly Leu Thr Thr Val Glu Ile Val Thr Met Ser
        755                 760                 765

His Gln Ala Leu Gly Asp Val Ala Gly Arg Gly Asn Glu Lys Lys Pro
        770                 775                 780

Ser Ser Val Arg Asp Tyr Lys Asp Asp Asp Lys His His His His
785                 790                 795                 800

His His

<210> SEQ ID NO 8
<211> LENGTH: 331
<212> TYPE: PRT
<213> ORGANISM: ARTIFICIAL
<220> FEATURE:
<223> OTHER INFORMATION: Fusion protein of abbreviated LDLR
      extracellular domain and hIgG1 Fc (with PCSK9 binding activity):
      LDLR-sECD-Fc (hIgG1) as a detection reagent

<400> SEQUENCE: 8

Met Glu Phe Gly Leu Ser Trp Leu Phe Leu Val Ala Ile Leu Lys Gly
1               5                   10                  15

Val Gln Cys Gly Thr Asn Glu Cys Leu Asp Asn Asn Gly Gly Cys Ser
            20                  25                  30

His Val Cys Asn Asp Leu Lys Ile Gly Tyr Glu Cys Leu Cys Pro Asp
        35                  40                  45

Gly Phe Gln Leu Val Ala Gln Arg Arg Cys Glu Asp Ile Asp Glu Cys
    50                  55                  60

Gln Asp Pro Asp Thr Cys Ser Gln Leu Cys Val Asn Leu Glu Gly Gly
65                  70                  75                  80

Tyr Lys Cys Gln Cys Glu Glu Gly Phe Gln Leu Asp Pro His Thr Lys
                85                  90                  95

Ala Cys Lys Glu Pro Lys Ser Ser Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Asp
225                 230                 235                 240

Glu Leu Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
```

```
                290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 9
<211> LENGTH: 294
<212> TYPE: PRT
<213> ORGANISM: ARTIFICIAL
<220> FEATURE:
<223> OTHER INFORMATION: Fusion protein of more truncated LDLR
      extracellular domain and hIgG1 Fc (with PCSK9 binding activity):
      LDLR-ssECD-Fc (hIgG1) as a detection reagent

<400> SEQUENCE: 9

Met Glu Phe Gly Leu Ser Trp Leu Phe Leu Val Ala Ile Leu Lys Gly
1               5                   10                  15

Val Gln Cys Gly Thr Asn Glu Cys Leu Asp Asn Asn Gly Gly Cys Ser
            20                  25                  30

His Val Cys Asn Asp Leu Lys Ile Gly Tyr Glu Cys Leu Cys Pro Asp
        35                  40                  45

Gly Phe Gln Leu Val Ala Gln Arg Arg Cys Glu Asp Ile Asp Glu Pro
    50                  55                  60

Lys Ser Ser Asp Lys Thr His Thr Cys Pro Pro Cys Pro Ala Pro Glu
65                  70                  75                  80

Leu Leu Gly Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
            100                 105                 110

Val Ser His Glu Asp Pro Glu Val Lys Phe Asn Trp Tyr Val Asp Gly
        115                 120                 125

Val Glu Val His Asn Ala Lys Thr Lys Pro Arg Glu Glu Gln Tyr Asn
    130                 135                 140

Ser Thr Tyr Arg Val Val Ser Val Leu Thr Val Leu His Gln Asp Trp
145                 150                 155                 160

Leu Asn Gly Lys Glu Tyr Lys Cys Lys Val Ser Asn Lys Ala Leu Pro
                165                 170                 175

Ala Pro Ile Glu Lys Thr Ile Ser Lys Ala Lys Gly Gln Pro Arg Glu
            180                 185                 190

Pro Gln Val Tyr Thr Leu Pro Pro Ser Arg Asp Glu Leu Thr Lys Asn
        195                 200                 205

Gln Val Ser Leu Thr Cys Leu Val Lys Gly Phe Tyr Pro Ser Asp Ile
    210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Lys
                245                 250                 255

Leu Thr Val Asp Lys Ser Arg Trp Gln Gln Gly Asn Val Phe Ser Cys
            260                 265                 270

Ser Val Met His Glu Ala Leu His Asn His Tyr Thr Gln Lys Ser Leu
        275                 280                 285

Ser Leu Ser Pro Gly Lys
    290

<210> SEQ ID NO 10
```

<211> LENGTH: 121
<212> TYPE: PRT
<213> ORGANISM: Murine
<220> FEATURE:
<223> OTHER INFORMATION: mAb-001 VH

<400> SEQUENCE: 10

Gln Val His Leu Gln Gln Ser Gly Ala Glu Leu Ala Lys Pro Gly Ala
1               5                   10                  15

Ser Val Lys Leu Ser Cys Lys Ala Ser Gly Tyr Thr Phe Asn Asp Tyr
            20                  25                  30

Trp Met His Trp Val Lys Glu Arg Pro Gly Gln Gly Leu Glu Trp Ile
        35                  40                  45

Gly Tyr Ile Asn Pro Ser Ser Gly Phe Thr Lys Tyr His Gln Asn Phe
    50                  55                  60

Lys Asp Lys Ala Thr Leu Thr Ala Asp Lys Ser Ser Thr Ala Tyr
65                  70                  75                  80

Met Gln Leu Ser Ser Leu Thr Tyr Asp Asp Ser Ala Val Tyr Tyr Cys
                85                  90                  95

Ala Arg Gln Tyr Asp Tyr Asp Glu Asp Trp Tyr Phe Asp Val Trp Gly
            100                 105                 110

Thr Gly Thr Thr Val Thr Val Ser Ser
        115                 120

<210> SEQ ID NO 11
<211> LENGTH: 112
<212> TYPE: PRT
<213> ORGANISM: Murine
<220> FEATURE:
<223> OTHER INFORMATION: mAb-001VL

<400> SEQUENCE: 11

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Phe Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Arg Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Phe Asn Leu Phe Thr Phe Gly Ser Gly Thr Lys Leu Glu Ile Lys
            100                 105                 110

<210> SEQ ID NO 12
<211> LENGTH: 5
<212> TYPE: PRT
<213> ORGANISM: Murine
<220> FEATURE:
<223> OTHER INFORMATION: mAb-001 HCDR1

<400> SEQUENCE: 12

Asp Tyr Trp Met His
1               5

<210> SEQ ID NO 13
<211> LENGTH: 17

```
<212> TYPE: PRT
<213> ORGANISM: Murine
<220> FEATURE:
<223> OTHER INFORMATION: mAb-001 HCDR2

<400> SEQUENCE: 13

Tyr Ile Asn Pro Ser Ser Gly Phe Thr Lys Tyr His Gln Asn Phe Lys
1               5                   10                  15

Asp

<210> SEQ ID NO 14
<211> LENGTH: 12
<212> TYPE: PRT
<213> ORGANISM: Murine
<220> FEATURE:
<223> OTHER INFORMATION: mAb-001 HCDR3

<400> SEQUENCE: 14

Gln Tyr Asp Tyr Asp Glu Asp Trp Tyr Phe Asp Val
1               5                   10

<210> SEQ ID NO 15
<211> LENGTH: 17
<212> TYPE: PRT
<213> ORGANISM: Murine
<220> FEATURE:
<223> OTHER INFORMATION: mAb-001 LCDR1

<400> SEQUENCE: 15

Lys Ser Ser Gln Ser Leu Leu Asn Ser Arg Thr Arg Lys Asn Phe Leu
1               5                   10                  15

Ala

<210> SEQ ID NO 16
<211> LENGTH: 7
<212> TYPE: PRT
<213> ORGANISM: Murine
<220> FEATURE:
<223> OTHER INFORMATION: mAb-001 LCDR2

<400> SEQUENCE: 16

Trp Ala Ser Thr Arg Glu Ser
1               5

<210> SEQ ID NO 17
<211> LENGTH: 8
<212> TYPE: PRT
<213> ORGANISM: Murine
<220> FEATURE:
<223> OTHER INFORMATION: mAb-001 LCDR3

<400> SEQUENCE: 17

Lys Gln Ser Phe Asn Leu Phe Thr
1               5

<210> SEQ ID NO 18
<211> LENGTH: 121
<212> TYPE: PRT
<213> ORGANISM: ARTIFICIAL
<220> FEATURE:
<223> OTHER INFORMATION: h001-VH.1

<400> SEQUENCE: 18

Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Asp Tyr
            20                  25                  30

Trp Met His Trp Val Arg Gln Ala Pro Gly Gln Gly Leu Glu Trp Met
            35                  40                  45

Gly Tyr Ile Asn Pro Ser Ser Gly Phe Thr Lys Tyr His Gln Asn Phe
50                  55                  60

Lys Asp Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Gln Tyr Asp Tyr Asp Glu Asp Trp Tyr Phe Asp Val Trp Gly
            100                 105                 110

Gln Gly Thr Thr Val Thr Val Ser Ser
            115                 120

<210> SEQ ID NO 19
<211> LENGTH: 121
<212> TYPE: PRT
<213> ORGANISM: ARTIFICIAL
<220> FEATURE:
<223> OTHER INFORMATION: h001-VH.1A

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Asp Tyr
            20                  25                  30

Trp Met His Trp Val Arg Gln Ala Pro Gly Gln Gly Leu Glu Trp Met
            35                  40                  45

Gly Tyr Ile Asn Pro Ser Ser Gly Phe Thr Lys Tyr His Gln Asn Phe
50                  55                  60

Lys Asp Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Gln Tyr Asp Tyr Asp Glu Asp Trp Tyr Phe Asp Val Trp Gly
            100                 105                 110

Gln Gly Thr Thr Val Thr Val Ser Ser
            115                 120

<210> SEQ ID NO 20
<211> LENGTH: 121
<212> TYPE: PRT
<213> ORGANISM: ARTIFICIAL
<220> FEATURE:
<223> OTHER INFORMATION: h001-VH.1B

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Trp Met His Trp Val Arg Gln Ala Pro Gly Gln Gly Leu Glu Trp Met
            35                  40                  45

Gly Tyr Ile Asn Pro Ser Ser Gly Phe Thr Lys Tyr His Gln Asn Phe
50                  55                  60

Lys Asp Arg Val Thr Met Thr Arg Asp Thr Ser Ile Ser Thr Ala Tyr
65                  70                  75                  80

Met Glu Leu Ser Arg Leu Thr Ser Asp Asp Thr Ala Val Tyr Tyr Cys
            85                  90                  95

Ala Arg Gln Tyr Asp Tyr Asp Glu Asp Trp Tyr Phe Asp Val Trp Gly
            100                 105                 110

Gln Gly Thr Thr Val Thr Val Ser Ser
            115                 120

<210> SEQ ID NO 21
<211> LENGTH: 121
<212> TYPE: PRT
<213> ORGANISM: ARTIFICIAL
<220> FEATURE:
<223> OTHER INFORMATION: h001-VH.1C

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Asp Tyr
            20                  25                  30

Trp Met His Trp Val Arg Gln Ala Pro Gly Gln Gly Leu Glu Trp Met
            35                  40                  45

Gly Tyr Ile Asn Pro Ser Ser Gly Phe Thr Lys Tyr His Gln Asn Phe
        50                  55                  60

Lys Asp Arg Val Thr Met Thr Arg Asp Thr Ser Ile Ser Thr Ala Tyr
65                  70                  75                  80

Met Glu Leu Ser Arg Leu Thr Ser Asp Asp Thr Ala Val Tyr Tyr Cys
            85                  90                  95

Ala Arg Gln Tyr Asp Tyr Asp Glu Asp Trp Tyr Phe Asp Val Trp Gly
            100                 105                 110

Gln Gly Thr Thr Val Thr Val Ser Ser
            115                 120

<210> SEQ ID NO 22
<211> LENGTH: 121
<212> TYPE: PRT
<213> ORGANISM: ARTIFICIAL
<220> FEATURE:
<223> OTHER INFORMATION: h001-VH.1D

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Asp Tyr
            20                  25                  30

Trp Met His Trp Val Arg Gln Ala Pro Gly Gln Gly Leu Glu Trp Met
            35                  40                  45

Gly Tyr Ile Asn Pro Ser Ser Gly Phe Thr Lys Tyr His Gln Asn Phe
        50                  55                  60

Lys Asp Arg Val Thr Met Thr Ala Asp Lys Ser Ile Ser Thr Ala Tyr
65                  70                  75                  80

Met Glu Leu Ser Arg Leu Thr Ser Asp Asp Thr Ala Val Tyr Tyr Cys
            85                  90                  95

Ala Arg Gln Tyr Asp Tyr Asp Glu Asp Trp Tyr Phe Asp Val Trp Gly
            100                 105                 110

Gln Gly Thr Thr Val Thr Val Ser Ser
            115                 120

```
<210> SEQ ID NO 23
<211> LENGTH: 121
<212> TYPE: PRT
<213> ORGANISM: ARTIFICIAL
<220> FEATURE:
<223> OTHER INFORMATION: h001-VH.1E

<400> SEQUENCE: 23

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Asn Asp Tyr
            20                  25                  30

Trp Met His Trp Val Lys Gln Ala Pro Gly Gln Gly Leu Glu Trp Ile
        35                  40                  45

Gly Tyr Ile Asn Pro Ser Ser Gly Phe Thr Lys Tyr His Gln Asn Phe
    50                  55                  60

Lys Asp Lys Ala Thr Leu Thr Ala Asp Lys Ser Ile Ser Thr Ala Tyr
65                  70                  75                  80

Met Glu Leu Ser Arg Leu Thr Ser Asp Thr Ala Val Tyr Tyr Cys
                85                  90                  95

Ala Arg Gln Tyr Asp Tyr Asp Glu Asp Trp Tyr Phe Asp Val Trp Gly
            100                 105                 110

Gln Gly Thr Thr Val Thr Val Ser Ser
            115                 120

<210> SEQ ID NO 24
<211> LENGTH: 112
<212> TYPE: PRT
<213> ORGANISM: ARTIFICIAL
<220> FEATURE:
<223> OTHER INFORMATION: h001-VL.1 (CDR grafting)

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Arg Thr Arg Lys Asn Phe Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Lys Gln
                85                  90                  95

Ser Phe Asn Leu Phe Thr Phe Gly Gln Gly Thr Lys Leu Glu Ile Lys
            100                 105                 110

<210> SEQ ID NO 25
<211> LENGTH: 112
<212> TYPE: PRT
<213> ORGANISM: ARTIFICIAL
<220> FEATURE:
<223> OTHER INFORMATION: h001-VL.1A

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30
```

-continued

Arg Thr Arg Lys Asn Phe Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Lys Gln
                85                  90                  95

Ser Phe Asn Leu Phe Thr Phe Gly Gln Gly Thr Lys Leu Glu Ile Lys
            100                 105                 110

<210> SEQ ID NO 26
<211> LENGTH: 112
<212> TYPE: PRT
<213> ORGANISM: ARTIFICIAL
<220> FEATURE:
<223> OTHER INFORMATION: h001-VL.1B

<400> SEQUENCE: 26

Asp Ile Gln Met Ser Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
                20                  25                  30

Arg Thr Arg Lys Asn Phe Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Lys Gln
                85                  90                  95

Ser Phe Asn Leu Phe Thr Phe Gly Gln Gly Thr Lys Leu Glu Ile Lys
            100                 105                 110

<210> SEQ ID NO 27
<211> LENGTH: 112
<212> TYPE: PRT
<213> ORGANISM: ARTIFICIAL
<220> FEATURE:
<223> OTHER INFORMATION: h001-VL.1C

<400> SEQUENCE: 27

Asp Ile Val Met Ser Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
                20                  25                  30

Arg Thr Arg Lys Asn Phe Leu Ala Trp Tyr Gln Gln Lys Pro Gly Lys
            35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Lys Gln
                85                  90                  95

Ser Phe Asn Leu Phe Thr Phe Gly Gln Gly Thr Lys Leu Glu Ile Lys
            100                 105                 110

<210> SEQ ID NO 28
<211> LENGTH: 451
<212> TYPE: PRT
<213> ORGANISM: ARTIFICIAL
<220> FEATURE:
<223> OTHER INFORMATION: h001-4-IgG1 Heavy chain amino acid sequence

<400> SEQUENCE: 28

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Asp Tyr
            20                  25                  30

Trp Met His Trp Val Arg Gln Ala Pro Gly Gln Gly Leu Glu Trp Met
        35                  40                  45

Gly Tyr Ile Asn Pro Ser Ser Gly Phe Thr Lys Tyr His Gln Asn Phe
    50                  55                  60

Lys Asp Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gln Tyr Asp Tyr Asp Glu Asp Trp Tyr Phe Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu

```
            370                 375                 380
Trp Glu Ser Asn Gly Gln Pro Glu Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 29
<211> LENGTH: 1413
<212> TYPE: DNA
<213> ORGANISM: ARTIFICIAL
<220> FEATURE:
<223> OTHER INFORMATION: h001-4-IgG1 Heavy chain DNA sequence

<400> SEQUENCE: 29
atggagtttg gctgagctg gctttttctt gtcgcgattc ttaagggtgt ccagtgccag      60
gtgcagctgg tgcagagcgg cgctgaggtg aagaagcccg gagcgagcgt aaaggtgagc     120
tgcaaggcca gcggatacac cttcaccgac tactggatgc actgggtgag gcaggcccca     180
ggacagggcc tggagtggat gggctacatc aaccccagca gcggctttac caagtatcac     240
cagaacttca agacagggt gaccatgacc agggacacca gcatcagcac cgcctacatg      300
gagctgagca ggctgaggag cgacgacacc gccgtgtact actgcgccag caatacgac      360 tacgacgagg actggtactt cgacgtgtgg ggccaaggaa ccaccgtgac tgtgagcagc     420
gcttcgacca agggcccatc ggtcttcccc ctggcaccct cctccaagag cacctctggg     480
ggcacagcgg ccctgggctg cctggtcaag gactacttcc ccgaaccggt gacggtgtcg     540
tggaactcag gcgccctgac cagcggcgtg cacaccttcc cggctgtcct acagtcctca     600
ggactctact ccctcagcag cgtggtgacc gtgccctcca gcagcttggg cacccagacc     660
tacatctgca acgtgaatca caagcccagc aacaccaagg tggacaagaa agttgagccc     720
aaatcttgtg acaaaactca cacatgccca ccgtgcccag cacctgaact cctgggggga     780
ccgtcagtct tcctcttccc cccaaaaccc aaggacaccc tcatgatctc ccggacccct     840
gaggtcacat gcgtggtggt ggacgtgagc cacgaagacc ctgaggtcaa gttcaactgg     900
tacgtggacg gcgtggaggt gcataatgcc aagacaaagc cgcgggagga gcagtacaac     960
agcacgtacc gtgtggtcag cgtcctcacc gtcctgcacc aggactggct gaatggcaag    1020
gagtacaagt gcaaggtctc caacaaagcc ctcccagccc ccatcgagaa aaccatctcc    1080
aaagccaaag gcagccccg agaaccacag gtgtacaccc tgcccccatc ccgggatgag    1140
ctgaccaaga accaggtcag cctgacctgc ctggtcaaag gcttctatcc agcgacatc    1200 gccgtggagt gggagagcaa tgggcagccg gagaacaact acaagaccac gcctcccgtg    1260
ctggactccg acggctcctt cttcctctac agcaagctca ccgtggacaa gagcaggtgg    1320
cagcagggga acgtcttctc atgctccgtg atgcatgagg ctctgcacaa ccactacacg    1380
cagaagagcc tctccctgtc tccgggtaaa tga                                 1413

<210> SEQ ID NO 30
<211> LENGTH: 219
<212> TYPE: PRT
```

<213> ORGANISM: ARTIFICIAL
<220> FEATURE:
<223> OTHER INFORMATION: h001-4-kappa Light chain amino acid sequence

<400> SEQUENCE: 30

Asp Ile Val Met Ser Gln Ser Pro Ser Leu Ser Ala Ser Val Gly
1               5                   10                  15

Asp Arg Val Thr Ile Thr Cys Lys Ser Gln Ser Leu Leu Asn Ser
            20                  25                  30

Arg Thr Arg Lys Asn Phe Leu Ala Trp Tyr Gln Gln Lys Pro Gly Lys
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Lys Gln
                85                  90                  95

Ser Phe Asn Leu Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 31
<211> LENGTH: 726
<212> TYPE: DNA
<213> ORGANISM: ARTIFICIAL
<220> FEATURE:
<223> OTHER INFORMATION: h001-4-kappa Light chain DNA sequence

<400> SEQUENCE: 31
atggacatgc gcgtgcccgc ccagctgctg ggcctgctgc tgctgtggtt ccccggctcg     60
cgatgcgaca tcgtgatgtc tcagagccca tctagcctga gcgccagcgt gggcgacagg    120
gtaaccatca cctgcaagag cagccaaagc ctgctgaaca gcaggacccg caagaacttc    180
ctggcttggt atcagcagaa gcccggcaag tctcccaagt tgctgatcta ctgggccagc    240
accagggaga gcggcgtgcc cgacaggttc agcggctccg gcagcggcac cgacttcacc    300
ctgaccatct ctagtctgca gcccgaggac ttcgccacct actactgcaa gcagagcttc    360
aatctgttca ccttcggcca gggcaccaag ctggagatca gcgtacggt ggctgcacca    420 tctgtcttca tcttcccgcc atctgatgag cagttgaaat ctggaactgc ctctgttgtg    480
tgcctgctga ataacttcta tcccagagag gccaaagtac agtggaaggt ggataacgcc    540
ctccaatcgg gtaactccca ggagagtgtc acagagcagg acagcaagga cagcacctac    600
agcctcagca gcaccctgac gctgagcaaa gcagactacg agaaacacaa agtctacgcc    660

```
tgcgaagtca cccatcaggg cctgagctcg cccgtcacaa agagcttcaa caggggagag    720
tgttga                                                               726
```

<210> SEQ ID NO 32
<211> LENGTH: 451
<212> TYPE: PRT
<213> ORGANISM: ARTIFICIAL
<220> FEATURE:
<223> OTHER INFORMATION: h001-4-IgG1-YTE Heavy chain amino acid sequence

<400> SEQUENCE: 32

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Trp Met His Trp Val Arg Gln Ala Pro Gly Gln Gly Leu Glu Trp Met
        35                  40                  45

Gly Tyr Ile Asn Pro Ser Ser Gly Phe Thr Lys Tyr His Gln Asn Phe
    50                  55                  60

Lys Asp Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gln Tyr Asp Tyr Asp Glu Asp Trp Tyr Phe Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Tyr
                245                 250                 255

Ile Thr Arg Glu Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
```

```
                    340                 345                 350
Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 33
<211> LENGTH: 1413
<212> TYPE: DNA
<213> ORGANISM: ARTIFICIAL
<220> FEATURE:
<223> OTHER INFORMATION: h001-4-IgG1-YTE Heavy chain DNA sequence

<400> SEQUENCE: 33
atggagtttg ggctgagctg gcttttcctt gtcgcgattc ttaagggtgt ccagtgccag      60
gtgcagctgg tgcagagcgg cgctgaggtg aagaagcccg gagcgagcgt aaaggtgagc    120
tgcaaggcca gcggatacac cttcaccgac tactggatgc actgggtgag gcaggcccca    180
ggacagggcc tggagtggat gggctacatc aacccccagca gcggctttac caagtatcac    240
cagaacttca agacagggt gaccatgacc agggacacca gcatcagcac cgcctacatg    300
gagctgagca ggctgaggag cgacgacacc gccgtgtact actgcgccag caatacgac    360 tacgacgagg actggtactt cgacgtgtgg ggccaaggaa ccaccgtgac tgtgagcagc    420
gcttcgacca agggcccatc ggtcttcccc ctggcaccct cctccaagag cacctctggg    480
ggcacagcgg ccctgggctg cctggtcaag gactacttcc ccgaaccggt gacggtgtcg    540
tggaactcag gcgccctgac cagcggcgtg cacaccttcc cggctgtcct acagtcctca    600
ggactctact ccctcagcag cgtggtgacc gtgccctcca gcagcttggg cacccagacc    660
tacatctgca acgtgaatca caagcccagc aacaccaagg tggacaagaa agttgagccc    720
aaatcttgtg acaaaactca cacatgccca ccgtgcccag cacctgaact cctgggggga    780
ccgtcagtct tcctcttccc cccaaaaccc aaggacaccc tctacatcac ccggagcct    840 gaggtcacat gcgtggtggt ggacgtgagc cacgaagacc ctgaggtcaa gttcaactgg    900
tacgtggacg gcgtggaggt gcataatgcc aagacaaagc cgcgggagga gcagtacaac    960
agcacgtacc gtgtggtcag cgtcctcacc gtcctgcacc aggactggct gaatggcaag   1020
gagtacaagt gcaaggtctc caacaaagcc ctcccagccc catcgagaa aaccatctcc   1080 aaagccaaag gcagccccg agaaccacag gtgtacaccc tgcccccatc ccgggatgag   1140
ctgaccaaga accaggtcag cctgacctgc ctggtcaaag gcttctatcc cagcgacatc   1200
gccgtggagt gggagagcaa tgggcagccg gagaacaact acaagaccac gcctcccgtg   1260
ctggactccg acggctcctt cttcctctac agcaagctca ccgtggacaa gagcaggtgg   1320
cagcagggga acgtcttctc atgctccgtg atgcatgagg ctctgcacaa ccactacacg   1380
```

```
cagaagagcc tctccctgtc tccgggtaaa tga                                    1413
```

PCSK9 ANTIBODY, ANTIGEN-BINDING FRAGMENT THEREOF, AND MEDICAL APPLICATION THEREOF

CROSS REFERENCE TO RELATED APPLICATIONS

This application is a Section 371 of International Application No. PCT/CN2016/111053, which was published in the Chinese Language on Jul. 6, 2017, under International Publication No. WO 2017/114230 A1, which claims priority to Chinese Patent Application No. 201511024618.2, filed on Dec. 31, 2015. Each disclosure is incorporated herein by reference in its entirety.

REFERENCE TO SEQUENCE LISTING SUBMITTED ELECTRONICALLY

This application contains a sequence listing, which is submitted electronically via EFS-Web as an ASCII formatted sequence listing with a file name "688452_75US Sequence Listing" and a creation date of Jun. 26, 2018, and having a size of 78 kb. The sequence listing submitted via EFS-Web is part of the specification and is herein incorporated by reference in its entirety.

FIELD OF THE INVENTION

The present invention relates to a PCSK9 antibody, antigen-binding fragments thereof, chimeric antibodies and humanized antibodies comprising the CDR regions of the PCSK9 antibody, as well as pharmaceutical compositions comprising the PCSK9 antibody and antigen-binding fragments thereof, as well as its use as a medicament for lowering the level of blood lipid.

BACKGROUND OF THE INVENTION

Hypercholesterolemia is a disease with abnormal metabolism of lipid, characterized in an increased level of serum cholesterol. Its main manifestation is the increased level of serum cholesterol, which causes cholesterol aggregation in vessels and consequently results in atherosclerosis formed. Abundant clinical and experimental research results have proven that the abnormal metabolism of lipid is closely correlated with occurrence and development of coronary heart disease. Therefore, reducing the concentration of cholesterol in blood becomes a main means for treating and preventing atherosclerosis.

With the rapid improvement of the national standard of living in China, dyslipidemia is becoming a main factor endangering urban and rural residents of China. According to the statistic results in 2012, about 40% of deaths per year in China were attributed to cardiovascular diseases. The morbidity of dyslipidemia in adults in China is 18.6%, and it is estimated now that 160 million people have dyslipidemia. The morbidities of different types of dyslipidemia are as follows: 2.9% for hypercholesterolemia, 11.9% for hypertriglyceridemia, 7.4% for low high density lipoproteinemia, and 3.9% for marginally increased blood cholesterol level. It was mentioned that there are 33 million people having hypercholesterolemia in China, however, for local areas, the morbidity of dyslipidemia is far more serious than the above data, Chronic Disease Prevention and Control China Expert Consensus, by Chronic Disease Prevention and Control Branch from Disease Prevention and Control Committee, Ministry of Public Health, 2012.

At present, the medicaments clinically used for controlling lipid levels are mainly focused on statins. Lipitor, as a most widely used and a best-selling cholesterol-lowering medicament, reduces the production of cholesterol by blocking the effect of cholesterol-producing enzymes in the liver, and therefore increases the uptake of cholesterol from blood by the liver, so that reduces the concentration of cholesterol in blood. However, Lipitor has disadvantages. Firstly it will be understood from data, Lipitor can reduce low density lipoprotein by 30% to 40%, however, an effectively reduced blood lipid level still cannot be achieved in many patients (low density lipoprotein<50 mg/dL). Secondly, there is racial difference among patients in response rate to Lipitor. Because of these reasons, the patients need a more effective medicine for reducing blood lipid.

Familial hypercholesterolemia (FM) is an autosomal single-gene dominant hereditary disease, clinical features of which are significantly increased total cholesterol (TC) and low density lipoprotein-cholesterol (LDL-c) in blood, xanthelasmata, corneal arcus and premature cardiovascular disease. Mutation in the low density lipoprotein receptor (LDL receptor, LDLR) gene causes LDLR deficiency or absence, consequently LDL-c will not be transported to liver to be cleaned, and hence the level of LDL-c in blood is increased. Currently three (3) genes have been identified to be correlated with occurrence of FM. They are LDLR gene, apolipoprotein B100 gene and proprotein convertase subtilisin/kexin type 9 (PCSK9) gene, respectively.

Proprotein convertase subtilisin/kexin type 9 (PCSK9) is a proprotein convertase, which is a subfamily of protease K belonging to the secretory *Bacillus subtilis* family. The encoded protein is synthesized as a soluble proenzyme, and is intra-molecularly processed in the endoplasmic reticulum by self-catalyzing. According to experimental results, PCSK9 promotes degradation of LDL receptor and thus increases the amount of LDL cholesterol in plasma, while LDL receptor mediates the endocytosis process of LDL in liver, and the latter is a main pathway to remove LDL from the circulating system. Researchers have found that PCSK9 gene mutations were identified in 12.5% of hypercholesterolemia (ADH) patients. There are various types of PCSK9 mutations. According to different influences of mutations on LDL-c level regulated by PCSK9, the mutations can be divided into two groups, loss-of-function type and gain-of-function type. Loss-of-function mutations are associated with low blood cholesterol level and have an effect on preventing occurrence of atherosclerotic heart disease. The rates of PCSK9 mutations associated with low cholesterol are higher in population of Africans than those in other races. PCSK9 gain-of-function mutations raise plasma cholesterol level by increasing PCSK9 function and reducing LDLR expression, which will cause serious hypercholesterolemia and premature coronary atherosclerotic heart disease. It is found at present that PCSK9 gain-of-function mutations include D374Y, S127R, F216L, N157K, R306S and so on. In comparison with the PCSK9 wild type, in D374Y mutants, the LDLR on the cell surface was decreased by 36%, and in S127R mutants was decreased by 10%.

As a potential new target, PCSK9 has become a hot topic in research of hypercholesterolemia. It is important to further understand the mechanism of cholesterol metabolism and find new therapeutic strategies. Many multinational pharmaceutical companies are developing monoclonal antibodies against PCSK9, which increase the concentration of LDLR on the liver surface and reduce the concentration of LDL in blood by neutralizing PCSK9 in blood. The relevant patents and patent applications are WO2011111007, WO2011072263, WO2013170367, WO2013169886, WO2013148284, WO2013091103, WO2013039958, WO2013039969, WO2013016648, WO2013008185, WO2012170607, WO2012168491, WO2012154999, WO2012109530, WO2012101251, WO2012088313, U.S. Pat. No. 8,829,165B2, U.S. Pat. No. 8,563,698B2, U.S. Pat. No. 8,859,741B2, U.S. Pat. No. 8,871,913B2, U.S. Pat. No. 8,871,914B2, U.S. Pat. No. 8,883,983B2, WO2012058137 and WO2012054438.

This present invention provides PCSK9 antibodies with higher affinity, higher selectivity and higher bioactivity.

SUMMARY OF THE INVENTION

The present invention provides a PCSK9 antibody or an antigen-binding fragment thereof, comprising one or more CDRs selected from the following: a HCDR as shown in SEQ ID NO:12, SEQ ID NO:13 or SEQ ID NO: 14, or a HCDR as shown in sequence having at least 95% identity to SEQ ID NO:12, SEQ ID NO:13 or SEQ ID NO: 14; and a LCDR as shown in SEQ ID NO:15, SEQ ID NO:16 or SEQ ID NO: 17, or a LCDR as shown in sequence having at least 95% identity to SEQ ID NO:15, SEQ ID NO:16 or SEQ ID NO: 17.

In another preferred embodiment of the present invention, the PCSK9 antibody or the antigen-binding fragment thereof according to the present invention comprises a HCDR1, a HCDR2 and a HCDR3 as shown in SEQ ID NO: 12, SEQ ID NO: 13 and SEQ ID NO: 14, respectively; or comprises a HCDR1, a HCDR2 and a HCDR3 as shown in the sequence having at least 95% identity to SEQ ID NO: 12, SEQ ID NO: 13 and SEQ ID NO: 14, respectively.

In another preferred embodiment of the present invention, the PCSK9 antibody or the antigen-binding fragment thereof according to the present invention comprises a LCDR1, a LCDR2 and a LCDR3 as shown in SEQ ID NO: 15, SEQ ID NO: 16 and SEQ ID NO: 17, respectively; or comprises a LCDR1, a LCDR2 and a LCDR3 as shown in the sequence having at least 95% identity to SEQ ID NO: 15, SEQ ID NO: 16 and SEQ ID NO: 17, respectively.

The amino acid sequence having at least 95% identity can be obtained by inducing mutations in the CDR regions of the present invention by means of affinity maturation.

In another preferred embodiment of the present invention, the PCSK9 antibody or the antigen-binding fragment thereof according to the present invention is a murine antibody or fragment thereof.

In another preferred embodiment of the PCSK9 antibody or the antigen-binding fragment thereof according to the present invention, the PCSK9 antibody light chain variable region further comprises light chain FR regions derived from murine κ chain or a variant thereof, or light chain FR regions derived from murine λ chain or a variant thereof, the PCSK9 antibody heavy chain variable region further comprises heavy chain FR regions derived from murine IgG1 or a variant thereof, or heavy chain FR regions derived from murine IgG2 or a variant thereof, or heavy chain FR regions derived from murine IgG3 or a variant thereof.

In another preferred embodiment of the PCSK9 antibody or the antigen-binding fragment thereof according to the present invention, the murine antibody comprises the heavy chain variable sequence of SEQ ID NO: 10 and the light chain variable sequence of SEQ ID NO: 11.

In another preferred embodiment of the PCSK9 antibody or the antigen-binding fragment thereof according to the present invention, the PCSK9 antibody light chain further comprises light chain constant regions derived from murine κ chain or a variant thereof, or light chain constant regions derived from murine λ chain or a variant thereof; the PCSK9 antibody heavy chain further comprises heavy chain constant regions derived from murine IgG1 or a variant thereof, or heavy chain constant regions derived from murine IgG2 or a variant thereof, or heavy chain constant regions derived from murine IgG3 or a variant thereof.

In another preferred embodiment of the PCSK9 antibody or the antigen-binding fragment thereof according to the present invention, the antibody or antigen-binding fragment thereof is a chimeric antibody or fragment thereof.

In another preferred embodiment of the PCSK9 antibody or the antigen-binding fragment thereof according to the present invention, the antibody or antigen-binding fragment thereof is a humanized antibody or fragment thereof.

In another preferred embodiment of the PCSK9 antibody or the antigen-binding fragment thereof according to the present invention, the heavy chain FR sequence of the heavy chain variable region of the humanized antibody is derived from a combination sequence of human germline heavy chains IGHV1-2*02 and hjh2, and a mutant sequence thereof; preferably comprises a FR1, a FR2, a FR3 of human germline heavy chain IGHV1-2*02 and a FR4 of hjh2, and a mutant sequence thereof, or amino acid sequence having at least 95% identity to the sequences thereof.

In another preferred embodiment of the PCSK9 antibody or the antigen-binding fragment thereof according to the present invention, the humanized antibody contains a heavy chain variable region as shown in SEQ ID NO: 18 or a heavy chain variable region as shown in a variant of SEQ ID NO: 18; wherein the variant of SEQ ID NO: 18 is a sequence with 0-10 amino acid changes in the heavy chain variable region as shown in SEQ ID NO: 18. The amino acid changes can be made based on technology in the art for improving affinity or half-life, for example, modifying the amino acid of a CDR by using affinity maturation, or modifying the amino acid of a FR by using back-mutations.

In another preferred embodiment of the PCSK9 antibody or the antigen-binding fragment thereof according to the present invention, the heavy chain FR sequence of the humanized antibody has 0-10 amino acid back-mutations, preferably one or more back-mutations are selected from the group consisting of T30N, R87T, R72A, T74K, M48I, V68A, M70L, R38K and R67K.

In another preferred embodiment of the PCSK9 antibody or the antigen-binding fragment thereof according to the present invention, the humanized antibody contains a heavy chain variable region selected from the group consisting of SEQ ID NO: 19, SEQ ID NO: 20, SEQ ID NO: 21, SEQ ID NO: 22 and SEQ ID NO: 23.

In another preferred embodiment of the PCSK9 antibody or the antigen-binding fragment thereof according to the present invention, the light chain FR sequence of the light chain variable region of the humanized antibody is derived from a combination sequence of human germline light chains IGKV1-39*01 and hjk2.1 and the mutant sequence thereof, comprises a FR1, a FR2, a FR3 of IGKV1-39*01 and a FR4 of hjk2.1 and the mutant sequence thereof, or an amino acid sequence having at least 95% identity to sequences thereof.

In another preferred embodiment of the PCSK9 antibody or the antigen-binding fragment thereof according to the present invention, the humanized antibody further contains a light chain variable region as shown in SEQ ID NO: 24 or a light chain variable region as shown in a variant of SEQ ID NO: 24; the variant of SEQ ID NO: 24 has 1-10 amino acid changes in the light chain variable region as shown in SEQ ID NO:24. This amino acid change can be made based on technology in the art for improving affinity or half-life, for example, modifying the amino acid of a CDR by using affinity maturation, or modifying the amino acid of a FR by using back-mutations.

In another preferred embodiment of the PCSK9 antibody or the antigen-binding fragment thereof according to the present invention, the variant of SEQ ID NO: 24 has 0-10 amino acid back-mutations in the FR sequence of the light chain variable region as shown in SEQ ID NO: 24; preferably the back-mutation is selected from the group consisting of T5S, S66D, Q3V and A49S; preferably A49S.

In another preferred embodiment of the PCSK9 antibody or the antigen-binding fragment thereof according to the present invention, the humanized antibody comprises a light chain variable region selected from the group consisting of SEQ ID NO:25, SEQ ID NO: 26 and SEQ ID NO: 27.

In another preferred embodiment of the PCSK9 antibody or the antigen-binding fragment thereof according to the present invention, the humanized antibody comprises a heavy chain variable region and/or a light chain variable region, wherein the heavy chain variable region is selected from the group consisting of SEQ ID NO:19, SEQ ID NO: 20, SEQ ID NO: 21, SEQ ID NO: 22 and SEQ ID NO: 23, or the heavy chain variable region is selected from the group consisting of a sequence having at least 95% identity to SEQ ID NO:19, SEQ ID NO: 20, SEQ ID NO: 21, SEQ ID NO: 22 and SEQ ID NO: 23; the light chain variable region is selected from the group consisting of SEQ ID NO:25, SEQ ID NO: 26 and SEQ ID NO: 27, or the light chain variable region is selected from the group consisting of a sequence having at least 95% identity to SEQ ID NO:25, SEQ ID NO: 26 and SEQ ID NO: 27.

In another preferred embodiment of the PCSK9 antibody or the antigen-binding fragment thereof according to the present invention, the PCSK9 antibody comprises a heavy chain variable region and a light chain variable region selected from the group consisting of:

1) the heavy chain variable region of SEQ ID NO: 18 and the light chain variable region of SEQ ID NO: 25;
2) the heavy chain variable region of SEQ ID NO: 18 and the light chain variable region of SEQ ID NO: 26;
3) the heavy chain variable region of SEQ ID NO: 18 and the light chain variable region of SEQ ID NO: 27;
4) the heavy chain variable region of SEQ ID NO: 19 and the light chain variable region of SEQ ID NO: 24;
5) the heavy chain variable region of SEQ ID NO: 19 and the light chain variable region of SEQ ID NO: 25;
6) the heavy chain variable region of SEQ ID NO: 19 and the light chain variable region of SEQ ID NO: 26;
7) the heavy chain variable region of SEQ ID NO: 19 and the light chain variable region of SEQ ID NO: 27;
8) the heavy chain variable region of SEQ ID NO: 20 and the light chain variable region of SEQ ID NO: 24;
9) the heavy chain variable region of SEQ ID NO: 20 and the light chain variable region of SEQ ID NO: 25;
10) the heavy chain variable region of SEQ ID NO: 20 and the light chain variable region of SEQ ID NO: 26;
11) the heavy chain variable region of SEQ ID NO: 20 and the light chain variable region of SEQ ID NO: 27;
12) the heavy chain variable region of SEQ ID NO: 21 and the light chain variable region of SEQ ID NO: 24;
13) the heavy chain variable region of SEQ ID NO: 21 and the light chain variable region of SEQ ID NO: 25;
14) the heavy chain variable region of SEQ ID NO: 21 and the light chain variable region of SEQ ID NO: 26;
15) the heavy chain variable region of SEQ ID NO: 21 and the light chain variable region of SEQ ID NO: 27;
16) the heavy chain variable region of SEQ ID NO: 22 and the light chain variable region of SEQ ID NO: 24;
17) the heavy chain variable region of SEQ ID NO: 22 and the light chain variable region of SEQ ID NO: 25;
18) the heavy chain variable region of SEQ ID NO: 22 and the light chain variable region of SEQ ID NO: 26;
19) the heavy chain variable region of SEQ ID NO: 22 and the light chain variable region of SEQ ID NO: 27;
20) the heavy chain variable region of SEQ ID NO: 23 and the light chain variable region of SEQ ID NO: 24;
21) the heavy chain variable region of SEQ ID NO: 23 and the light chain variable region of SEQ ID NO: 25;
22) the heavy chain variable region of SEQ ID NO: 23 and the light chain variable region of SEQ ID NO: 26;
23) the heavy chain variable region of SEQ ID NO: 23 and the light chain variable region of SEQ ID NO: 27; and
24) the heavy chain variable region of SEQ ID NO: 18 and the light chain variable region of SEQ ID NO: 24.

In another preferred embodiment of the PCSK9 antibody or the antigen-binding fragment thereof according to the present invention, the heavy chain of the PCSK9 antibody further comprises heavy chain constant regions derived from human IgG1, IgG2, IgG3, or IgG4 or a variant thereof, or an amino acid sequence having at least 95% identity to sequences thereof; preferably comprises heavy chain constant regions derived from human IgG1, IgG2, or IgG4 or comprises heavy chain constant regions of IgG1, IgG2, or IgG4 variants which prolong the half-life of the antibody in the serum via an amino acid mutation, most preferably comprises heavy chain constant regions of IgG1, IgG2, or IgG4 into which a YTE mutation was introduced;

The light chain of the PCSK9 antibody further comprises a constant region derived from a human κ chain, a human λ chain, or a variant thereof, or an amino acid sequence having at least 95% identity to the sequences thereof.

In another preferred embodiment of the PCSK9 antibody or the antigen-binding fragment thereof according to the present invention, the humanized antibody comprises a heavy chain and a light chain selected from the group consisting of:

1) the heavy chain of SEQ ID NO: 28 and the light chain of SEQ ID NO: 30; and
2) the heavy chain of SEQ ID NO: 32 and the light chain of SEQ ID NO: 30.

The present invention further provides a pharmaceutical composition, comprising a therapeutically effective dosage of the PCSK9 antibody or the antigen-binding fragment thereof according to the invention, and one or more pharmaceutically acceptable carriers, diluents, or excipients.

The present invention further provides a nucleic acid molecule encoding the PCSK9 antibody or the antigen-binding fragment described above.

The present invention further provides an expression vector comprising the nucleic acid molecule as described above.

The present invention further provides a host cell transformed with the expression vector as described above, wherein the host cell is selected from the group consisting of a prokaryotic cell and a eukaryotic cell, preferably a eukaryotic cell, more preferably a mammalian cell.

The present invention further provides a use of the PCSK9 antibody or the antigen-binding fragment thereof, or the pharmaceutical composition according to the invention, in the preparation of a medicament for treatment of a PCSK9-mediated disease or disorder, wherein the disease or the disorder is preferably a cholesterol-related disease (including "serum cholesterol related diseases"); more preferably the disease or the disorder is selected from the group consisting of hypercholesterolemia, heart disease, metabolic syndrome, diabetes, coronary heart disease, stroke, cardiovascular disease, Alzheimer's disease and general dyslipidemia; most preferably hypercholesterolemia, dyslipidemia, atherosclerosis, CVD or coronary heart disease.

The exemplary diseases which can be diagnosed with the antibody according to the present invention include cholesterol related diseases (including "serum cholesterol related diseases"), which includes one or more diseases selected from hypercholesterolemia, heart disease, metabolic syndrome, diabetes, coronary heart disease, stroke, cardiovascular disease, Alzheimer's disease and general dyslipidemia (which is characterized in increased total serum cholesterol, increased LDL, increased triglyceride, increased very low density lipoprotein (VLDL) and/or decreased HDL).

On the one hand, the present invention provides a method of treating or preventing hypercholesterolemia and/or at least one symptom selected from dyslipidemia, atherosclerosis, cardiovascular disease (CVD) and coronary heart disease, wherein the method comprises administering an effective amount of a PCSK9 antibody to the individual. The present invention also provides use of an effective amount of PCSK9 antibody against extracellular or circulating PCSK9 in the preparation of a medicament, wherein the medicament is for treating or preventing hypercholesterolemia and/or at least one symptom selected from dyslipidemia, atherosclerosis, CVD or coronary heart disease.

DETAILED DESCRIPTION OF THE INVENTION

1. Definitions

Figure 1:
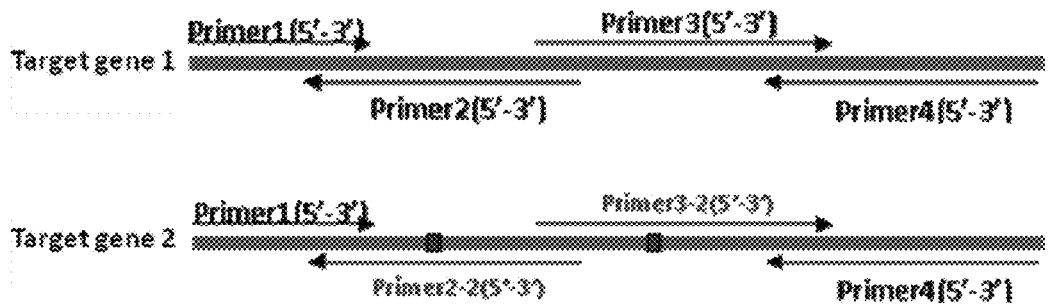
FIG. 1: A schematic of primer design for constructing vectors of the antibodies according to the present invention.

In order to more readily understand the invention, certain technical and scientific terms are specifically defined below. Unless specifically defined elsewhere in this document, all other technical and scientific terms used herein have the meaning commonly understood by one of ordinary skill in the art to which this invention belongs.

As used herein, the single-letter code and the three-letter code for amino acids are as described in J. Biol. Chem, 243, (1968) p 3558.

As used herein, "Antibody" refers to an immunoglobulin, a four-peptide chain structure connected together by disulfide bonds between two identical heavy chains and two identical light chains. Different immunoglobulin heavy chain constant regions exhibit different amino acid compositions and rank orders, hence they possess different kinds of antigenicity. Accordingly, immunoglobulins can be divided into five categories, or immunoglobulin isotypes, namely IgM, IgD, IgG IgA and IgE, the corresponding heavy chains are μ chain, δ chain, γ chain, α chain and ε chain, respectively. According to its amino acid composition of hinge region and the number and location of heavy chain disulfide bonds, the same type of Ig can be divided into different sub-types, for example, IgG can be divided into IgG1, IgG2, IgG3, and IgG4. The light chain can be divided into a κ or a λ chain according to different constant regions. Each of the five types of IgG can have a κ or λ chain.

In the present invention, the antibody light chain variable region mentioned herein further comprises a light chain constant region, which comprises a human or murine κ, λ chain, or a variant thereof.

In the present invention, the antibody heavy chain variable region mentioned herein further comprises a heavy chain constant region, which comprises a human or a murine IgG1, 2, 3, 4, or a variant thereof.

Near the N-terminus of the antibody heavy and light chains, about 110 of amino acids can vary greatly, known as a variable region (Fv region); the rest of the amino acids near the C-terminus are relatively stable, known as a constant region (C region). The variable region comprises three hypervariable regions (HVRs) and four relatively conserved framework regions (FRs). The three hypervariable regions determine the specificity of the antibody, also known as the complementarity determining region (CDR). Each light chain variable region (LCVR) and each heavy chain variable region (HCVR) is composed of three CDR regions and four FR regions, with the sequential order from the amino terminus to the carboxyl terminus being: FR1, CDR1, FR2, CDR2, FR3, CDR3, and FR4. Three light chain CDRs refer to LCDR1, LCDR2, and LCDR3; three heavy chain CDRs refer to HCDR1, HCDR2 and HCDR3. The number and location of CDR region amino acid residues in the LCVR and HCVR regions of the antibody or the antigen binding fragments herein comply with known Kabat numbering criteria (LCDR1-3, HCDE2-3), or comply with kabat and chothia numbering criteria (HCDR1).

The antibody of the present invention can comprise a murine antibody, a chimeric antibody and a humanized antibody, preferably a humanized antibody.

The term "murine antibody" in the present invention refers to an anti-human PCSK9 monoclonal antibody prepared according to the knowledge and skills in the field. During the preparation, a test object was injected with PCSK9 antigen, and then the hybridoma expressing the antibody which possesses desired sequences or functional characteristics was separated. In a preferred embodiment of the present invention, the murine PCSK9 antibody or the antigen binding fragment thereof, further comprises a light chain constant region of murine κ, λ chain, or a variant thereof, or further comprises a heavy chain constant region of murine IgG1, IgG2, IgG3, or IgG4, or a variant thereof.

The term "chimeric antibody" is an antibody which is formed by fusing the variable region of a murine antibody with the constant region of a human antibody, the chimeric antibody can alleviate the murine antibody-induced immune response. To establish a chimeric antibody, the hybridoma secreting a specific murine monoclonal antibody is first established, a variable region gene is cloned from the mouse hybridoma cells, then a constant region gene of a human antibody is cloned as desired, the mouse variable region gene is ligated with the human constant region gene to form a chimeric gene which can be inserted into a human vector, and finally the chimeric antibody molecule is expressed in the eukaryotic or prokaryotic industrial system. In a preferred embodiment of the present invention, the light chain of the PCSK9 chimeric antibody further comprises the light chain Fc regions of human κ, λ chain, or a variant thereof. The heavy chain of the PCSK9 chimeric antibody further comprises the heavy chain Fc regions of human IgG1, IgG2, IgG3, or IgG4, or a variant thereof, preferably comprises the heavy chain constant region of human IgG1, IgG2, IgG3, or IgG4, or preferably comprises the heavy chain constant region of human IgG1, IgG2, or IgG4 variants with amino acid mutations (e.g., YTE mutations) to extend the half-time life of the antibody in serum.

The term "humanized antibody", also known as CDR-grafted antibody, refers to an antibody generated by grafting murine CDR sequences into a variable region framework of a human antibody, namely, a sequence of human germline antibody framework of a different type. A humanized antibody overcomes the disadvantage of the strong antibody response induced by the chimeric antibody, which carries a large amount of murine protein components. Such framework sequences can be obtained from a public DNA database covering germline antibody gene sequences or published references. For example, germline DNA sequences of human heavy and light chain variable region genes can be found in "VBase" human germline sequence database (available on web www.mrccpe.com.ac.uk/vbase), as well as can be found in Kabat, E A, et al, 1991 Sequences of Proteins of Immunological Interest, 5th Ed. To avoid the decrease in activity while the immunogenicity is decreased, the framework sequences in the variable region of the human antibody are subjected to minimal back mutations to maintain the activity. The humanized antibody of the present invention also comprises a humanized antibody to which CDR affinity maturation is performed by phage display.

In a preferred embodiment of the present invention, the murine CDR sequences of the PCSK9 humanized antibodies are selected from the group consisting of SEQ ID NOs: 12, 13, 14, 15, 16 and 17. The variable region frame of the human antibody is designed to be selected, wherein the light chain FR sequence of the light chain variable region of the antibody is derived from a combination sequence of human germline light chains IGKV1-39*01 and hjk2.1; wherein the heavy chain FR sequence of the heavy chain variable region of the antibody is derived from a combination sequence of human germline heavy chains IGHV1-2*02 and hjh2. In order to avoid the decrease of the activity caused by the decrease of immunogenicity, the variable region of the human antibody described herein can be subjected to minimal back mutations to maintain the activity of antibody.

"Antigen-binding fragment" in the present invention refers to a Fab fragment, a Fab' fragment, a F(ab')$_2$ fragment having antigen-binding activity, as well as a Fv fragment or a scFv fragment binding to human PCSK9; it comprises one or more CDR regions of antibodies described in the present invention, selected from the group consisting of SEQ ID NOs: 12 to SEQ ID NO: 17. A Fv fragment comprises a heavy chain variable region and a light chain variable region, without a constant region, and it is a minimal antibody fragment possessing all antigen-binding sites. Generally, a Fv antibody further comprises a polypeptide linker between the VH and VL domains, and is capable of forming a structure necessary for antigen binding. Also, different linkers can be used to connect the variable regions of two antibodies to form a polypeptide chain, referred to as a single chain antibody or single chain Fv (scFv). The term "binding to PCSK9" in this invention means that it's capable of interacting with human PCSK9. The term "antigen-binding sites" in the present invention, refers to discontinuous, three-dimensional sites on the antigen, recognized by the antibody or the antigen-binding fragment of the present invention.

The term "Fc region" herein is used to define a C-terminal region of an immunoglobulin heavy chain that contains at least a portion of the constant region. The term includes native sequence Fc regions and variant Fc regions. In one embodiment, human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991. The Fc region is essential to the effector functions of antibodies. The effector functions include initiating complement-dependent cytotoxicity (CDC), initiating phagocytosis and antibody-dependent cell-mediated cytotoxicity (ADCC), and transferring antibodies across cellular barriers by transcytosis. In addition, the Fc region is critical for maintaining the serum half-life of an antibody of class IgG (Ward and Ghetie, Ther. Immunol. 2:77-94 (1995)). Researchers have found that the serum half-life of an IgG antibody is mediated by binding of Fc to the neonatal Fc receptor (FcRn). FcRn is a heterodimer consisting of a transmembrane α chain and a soluble β chain (β2-microglobulin). U.S. Pat. No. 6,165,745 discloses a method of producing an antibody with a decreased biological half-life by introducing a mutation into the DNA segment encoding the antibody. The mutation includes amino acid substitutions at position 253, 310, 311, 433, or 434 of the Fc-hinge domain. U.S. Pat. No. 6,277,375 B1 discloses a composition comprising a mutant IgG molecule having an increased serum half-life relative to the wild-type IgG, wherein the mutant IgG molecule comprises the following amino acid substitutions: threonine to leucine at position 252, threonine to serine at position 254, or threonine to phenylalanine at position 256 (T252L, T254S, and T256F). A mutant IgG with amino acid substitutions at position 433, 435, or 436 is also disclosed. U.S. Pat. No. 6,528,624 discloses a variant of an antibody comprising IgG Fc region, wherein the variant comprises amino acid substitutions at one or more amino acid positions of the human IgG Fc region (positions 270, 322, 326, 327, 329, 331, 333, and 334). WO 02/060919 A2 discloses a modified IgG comprising an IgG constant domain comprising one or more amino acid modifications relative to a wild-type IgG constant domain, wherein the modified IgG has an increased half-life compared to the half-life of an IgG having the wild-type IgG constant domain, and wherein the one or more amino acid modifications are at one or more positions selected from the group consisting of positions 251, 253, 255, 285-290, 308-314, 385-389, and 428-435. Specifically, the "YTE" or "YTE mutation" described herein refers to mutation combination in the Fc regions of IgG 1 for promoting the binding between the Fc region and human FcRn, extending the serum half-life of the antibody in human. The YTE mutant contains a combination of three "YTE mutations" M252Y, S254T and T256E. Residue numbering is based on the EU numbering system, which is also referred to as the EU index, such as the numbering of IgG heavy chains in Kabat et al (refer to U.S. Pat. No. 7,658,921). Compared to wild-type antibodies, YTE mutant antibodies greatly extend the half-life of antibodies in serum, e.g., Dall'Acqua et al, J. Biol. Chem. 281: 23514-24 (2006) and U.S. Pat. No. 7,083,784.

Methods for producing and purifying antibodies and antigen-binding fragments are well known in the art and can be found, for example, in Antibody Experimental Technology Guide of Cold Spring Harbor, Chapters 5-8 and 15. For example, mice can be immunized with human PCSK9, or fragments thereof, and the resulting antibodies can then be renatured, purified and sequenced using conventional methods well known in the art. Antigen-binding fragments can also be prepared by conventional methods. The antibody or the antigen-binding fragments of the present invention is genetically engineered to introduce one or more human framework regions (FRs) to a non-human derived CDR. Human FR germline sequences can be obtained from ImMunoGeneTics (IMGT) via their website http://imgt.cines.fr, or from The Immunoglobulin FactsBook, 2001ISBN012441351.

The engineered antibody or antigen-binding fragments of the present invention can be prepared and purified using conventional methods. For example, cDNA sequences encoding a heavy chain (SEQ ID NO: 28) and a light chain (SEQ ID NO: 30) can be cloned and recombined into a GS expression vector. The recombined immunoglobulin expression vector can then be stably transfected into CHO cells. As a more recommended method well known in the art, mammalian expression systems will result in glycosylation of antibodies, typically at the highly conserved N-terminus in the Fc region. Stable clones can be obtained through expression of an antibody specifically binding to human PCSK9. Positive clones can be expanded in serum-free culture medium for antibody production in bioreactors. Culture medium, into which an antibody has been secreted, can be purified by conventional techniques. For example, the medium can be conveniently applied to a Protein A or G Sepharose FF column that has been equilibrated with adjusted buffer. The column is washed to remove nonspecific binding components. The bound antibody is eluted by PH gradient and antibody fragments are detected by SDS-PAGE, and then pooled. The antibody can be filtered and concentrated using common techniques. Soluble aggregate and multimers can be effectively removed by common techniques, including size exclusion or ion exchange. The obtained product can be immediately frozen, for example at −70° C., or can be lyophilized.

"Administration" and "treatment," when applying to an animal, human, experimental subject, cell, tissue, organ, or biological fluid, refer to contacting an exogenous pharmaceutical, therapeutic, diagnostic agent, or composition with the animal, human, subject, cell, tissue, organ, or biological fluid. "Administration" and "treatment" can refer, e.g., to therapeutic, pharmacokinetic, diagnostic, research, and experimental methods. Treatment of a cell encompasses contacting a reagent with the cell, as well as contacting a reagent with a fluid, where the fluid is in contact with the cell. "Administration" and "treatment" also means in vitro and ex vivo treatments, e.g., of a cell, by a reagent, diagnostic, binding compound, or by another cell. "Treatment," as it applies to a human, veterinary, or a research subject, refers to therapeutic treatment, prophylactic or preventative measures, to research and diagnostic applications.

"Treat" means to administer a therapeutic agent, such as a composition comprising any of the binding compounds of the present invention, internally or externally to a patient having one or more disease symptoms for which the agent has known therapeutic activity. Typically, the agent is administered in an amount effective to alleviate one or more disease symptoms in the treated patient or population, so as to induce the regression of or inhibit the progression of such symptom(s) to any clinically measurable degree. The amount of a therapeutic agent that is effective to alleviate any particular disease symptom (also referred to "therapeutically effective amount") may vary according to factors such as the disease state, age, and weight of the patient, and the ability of the drug to elicit a desired response in the patient. Whether a disease symptom has been alleviated can be assessed by any clinical measurement typically used by physicians or other skilled healthcare providers to assess the severity or progression status of that symptom. While an embodiment of the present invention (e.g., a treatment method or article of manufacture) may not be effective in alleviating the disease symptom(s) of interest in every patient, it should alleviate the target disease symptom(s) of interest in a statistically significant number of patients as determined by any statistical test known in the art such as the Student's t-test, the chi-square test, the U-test according to Mann and Whitney, the Kruskal-Wallis test (H-test), Jonckheere-Terpstra-test and the Wilcoxon-test.

"Conservative modifications" or "conservative replacement or substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide does not substantially alter biological activity (see, e.g., Watson et al. (1987) Molecular Biology of the Gene, The Benjamin/Cummings Pub. Co., p. 224 (4.sup.th Ed.)). In addition, substitutions of structurally or functionally similar amino acids are less likely to disrupt biological activity.

"Effective amount" encompasses an amount sufficient to ameliorate or prevent a symptom or sign of a medical condition. Effective amount also means an amount sufficient to allow or facilitate diagnosis. An effective amount for a particular patient or veterinary subject can vary depending on factors such as the condition being treated, the general health of the patient, the route and dose of administration and the severity of side effects. An effective amount can be the maximal dose or dosing protocol that avoids significant side effects or toxic effects.

"Exogenous" refers to substances that are produced outside an organism, cell, or human body, depending on the context. "Endogenous" refers to substances that are produced within a cell, organism, or human body, depending on the context.

"Homology" refers to sequence similarity between two polynucleotide sequences or between two polypeptides. When a position in both of the two compared sequences is occupied by the same base or amino acid monomer subunit, e.g., if a position in each of two DNA molecules is occupied by adenine, the molecules are homologous at that position. The percent of homology between two sequences is a function of the number of matching or homologous positions shared by the two sequences divided by the number of positions to be compared, then multiplying by 100. For example, if 6 of 10 positions in two sequences are matched or homologous when the sequences are optimally aligned, the two sequences are 60% homologous. Generally, the comparison is made when two sequences are aligned to give maximum percent homology.

As used herein, the expressions "cell," "cell line," and "cell culture" are used interchangeably and all such designations include progeny. Thus, the words "transformants" and "transformed cells" include the primary subject cell and cultures derived therefrom without considering the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, "polymerase chain reaction" or "PCR" refers to a procedure or technique in which minute amounts of a specific moiety of nucleic acid, RNA and/or DNA, are amplified as described in, e.g., U.S. Pat. No. 4,683,195. Generally, sequence information from the ends of the region of interest or beyond needs to be available, such that oligonucleotide primers can be designed; these primers will be identical or similar in sequence to corresponding strands of the template to be amplified. The 5' terminal nucleotides of the two primers can be identical with the ends of the material to be amplified. PCR can be used to amplify specific RNA sequences, specific DNA sequences from total genomic DNA, and cDNA transcribed from total cellular RNA, bacteriophage or plasmid sequences, etc. See generally Mullis et al. (1987) Cold Spring Harbor Symp. Ouant. Biol. 51:263; Erlich, ed., (1989) PCR TECHNOLOGY (Stockton Press, N.Y.). As used herein, PCR is considered as one, but not the only, example of a nucleic acid polymerase reaction method for amplifying a nucleic acid test sample, comprising the use of a known nucleic acid as a primer and a nucleic acid polymerase to amplify or generate a specific moiety of the nucleic acid.

"Optional" or "optionally" means that the event or situation that follows can but does not necessarily occur, and the description includes the instances in which the event or circumstance does or does not occur. For example, "optionally comprises 1-3 antibody heavy chain variable regions" means the antibody heavy chain variable region with specific sequence can be, but not necessarily be, present.

"Pharmaceutical composition" refers to one containing a mixture of one or more compounds according to the present invention or a physiologically/pharmaceutically acceptable salt or prodrug thereof with other chemical components, as well as additional components such as physiologically/pharmaceutically acceptable carriers and excipients. The pharmaceutical composition aims at promoting the administration to an organism, facilitating the absorption of the active ingredient and thereby exerting a biological effect.

EXAMPLES AND TESTS

Hereinafter, the present invention is further described with reference to examples. However, the scope of the present invention is not limited thereto. In the examples of the present invention where specific conditions are not described, the experiments are generally conducted under conventional conditions as described in Antibody Technology Laboratory Manual and Mecular Cloning Manual of Cold Spring Harbor, or under conditions proposed by the material or product manufacturers. Where the source of the reagents is not specifically given, the reagents are commercially available conventional reagents.

Example 1. Preparation of PCSK9 Antigen and Test Protein

Protein Design and Expression

Using Uniprot Proprotein convertase subtilisin/kexin type 9 (human PCSK9, Uniprot number: Q8MBP7) as the template for PCSK9 of the invention to design the amino acid sequences of the antigen and the test protein. Optionally, the PCSK9 protein was fused with different labels such as a his tag or a peptide promoting immunization such as PADRE peptide, then cloned into pTT5 vectors (Biovector, Cat #: 102762) or pTargeT vectors (promega, A1410), respectively, transiently expressed in 293 cells or stably expressed in CHO-S cells, and purified. Finally, the antigen and test protein of the invention were obtained.

PCSK9 with His tag: PCSK9-His6, used as an immunogen for immunizing mice or used as detection reagent.

SEQ ID NO: 1
<u>MGTVSSRRSWWPLPLLLLLLLLLGPAGARA</u>QEDEDGDYEELVLALRSEED
GLAEAPEHGTTATFHRCAKDPWRLPGTYVVVLKEETHLSQSERTARRLQA
QAARRGYLTKILHVFHGLLPGFLVKMSGDLLELALKLPHVDYIEEDSSVF
AQSIPWNLERITPPRYRADEYQPPDGGSLVEVYLLDTSIQSDHREIEGRV
MVTDFENVPEEDGTRFHRQASKCDSHGTHLAGVVSGRDAGVAKGASMRSL
RVLNCQGKGTVSGTLIGLEFIRKSQLVQPVGPLVVLLPLAGGYSRVLNAA
CQRLARAGVVLVTAAGNFRDDACLYSPASAPEVITVGATNAQDQPVTLGT
LGTNFGRCVDLFAPGEDIIGASSDCSTCFVSQSGTSQAAAHVAGIAAMML
SAEPELTLAELRQRLIHFSAKDVINEAWFPEDQRVLTPNLVAALPPSTHG
AGWQLFCRTVWSAHSGPTRMATAVARCAPDEELLSCSSFSRSGKRRGERM
EAQGGKLVCRAHNAFGGEGVYAIARCCLLPQANCSVHTAPPAEASMGTRV
HCHQQGHVLTGCSSHWEVEDLGTHKPPVLRPRGQPNQCVGHREASIHASC
CHAPGLECKVKEHGIPAPQEQVTVACEEGWTLTGCSALPGTSHVLGAYAV
DNTCVVRSRDVSTTGSTSEGAVTAVAICCRSRHLAQASQELQ*HHHHHH*

Note: Underlined sequence is a signal peptide, and italic part is His-tag sequence (His6-tag).

PCSK9 with PADRE peptide and His-tag: PCSK9-PADRE-His6, used as an immunogen, wherein the contained PADRE peptide can promote immunization;

SEQ ID NO: 3
<u>MGTVSSRRSWWPLPLLLLLLLLLGPAGARA</u>QEDEDGDYEELV
LALRSEEDGLAEAPEHGTTATFHRCAKDPWRLPGTYVVVLKE
ETHLSQSERTARRLQAQAARRGYLTKILHVFHGLLPGFLVKM
SGDLLELALKLPHVDYIEEDSSVFAQSIPWNLERITPPRYRADE
YQPPDGGSLVEVYLLDTSIQSDHREIEGRVMVTDFENVPEEDG

TRFHRQASKCDSHGTHLAGVVSGRDAGVAKGASMRSLRVLN

CQGKGTVSGTLIGLEFIRKSQLVQPVGPLVVLLPLAGGYSRVL

NAACQRLARAGVVLVTAAGNFRDDACLYSPASAPEVITVGA

TNAQDQPVTLGTLGTNFGRCVDLFAPGEDIIGASSDCSTCFV

SQSGTSQAAAHVAGIAAMMLSAEPELTLAELRQRLIHFSAKD

VINEAWFPEDQRVLTPNLVAALPPSTHGAGWQLFCRTVWSA

HSGPTRMATAVARCAPDEELLSCSSFSRSGKRRGERMEAQGG

KLVCRAHNAFGGEGVYAIARCCLLPQANCSVHTAPPAEASMG

TRVHCHQQGHVLTGCSSHWEVEDLGTHKPPVLRPRGQPNQC

VGHREASIHASCCHAPGLECKVKEHGIPAPQEQVTVACEEGW

TLTGCSALPGTSHVLGAYAVDNTCVVRSRDVSTTGSTSEGAV

TAVAICCRSRHLAQASQELQGSGAKFVAAWTLKAAA*HHHHHH*

Note: Underlined sequence is a signal peptide, double underlined sequence is a linker, the dashed line sequence is PADRE peptide, and italic part is the His6-tag.
A fusion protein of PCSK9 with TEV cleavage site and His tag: PCSK9-TEV-His6, N-PCSK9 (N terminal PCSK9 domain), used as an immunogen, can be obtained by digestion with TEV enzyme;

SEQ ID NO: 3
MGTVSSRRSWWPLPLLLLLLLLLGPAGARAQEDEDGDYEELVLALRSEED

GLAEAPEHGTTATFHRCAKDPWRLPGTYVVVLKEETHLSQSERTARRLQA

QAARRGYLTKILHVFHGLLPGFLVKMSGDLLELALKLPHVDYIEEDSSVF

AQSIPWNLERITPPRYRADEYQPPDGGSLVEVYLLDTSIQSDHREIEGRV

MVTDFENVPEEDGTRFHRQASKCDSHGTHLAGVVSGRDAGVAKGASMRSL

RVLNCQGKGTVSGTLIGLEFIRKSQLVQPVGPLVVLLPLAGGYSRVLNAA

CQRLARAGVVLVTAAGNFRDDACLYSPASAPEVITVGATNAQDQPVTLGT

LGTNFGRCVDLFAPGEDIIGASSDCSTCFVSQSGTSQAAAHVAGIAAMML

SAEPELTLAELRQRLIHFSAKDVINEAWFPEDQRVLTPNLVAALPPSTHE

NLYFQGAGWQLFCRTVWSAHSGPTRMATAVARCAPDEELLSCSSFSRSGK

RRGERMEAQGGKLVCRAHNAFGGEGVYAIARCCLLPQANCSVHTAPPAEA

SMGTRVHCHQQGHVLTGCSSHWEVEDLGTHKPPVLRPRGQPNQCVGHREA

SIHASCCHAPGLECKVKEHGIPAPQEQVTVACEEGWTLTGCSALPGTSHV

LGAYAVDNTCVVRSRDVSTTGSTSEGAVTAVAICCRSRHLAQASQELQ*HH*

*HHHH*

Note: Underlined sequence is a signal peptide, double underlined sequence is TEV cleavage site, and italic part is the His6-tag.
PCSK9-D374Y mutant protein, with His-tag: PCSK9-D374Y-His6, used as a detection reagent;

SEQ ID NO: 4
MGTVSSRRSWWPLPLLLLLLLLLGPAGARAQEDEDGDYEELVLALRSEED

GLAEAPEHGTTATFHRCAKDPWRLPGTYVVVLKEETHLSQSERTARRLQA

QAARRGYLTKILHVFHGLLPGFLVKMSGDLLELALKLPHVDYIEEDSSVF

AQSIPWNLERITPPRYRADEYQPPDGGSLVEVYLLDTSIQSDHREIEGRV

MVTDFENVPEEDGTRFHRQASKCDSHGTHLAGVVSGRDAGVAKGASMRSL

RVLNCQGKGTVSGTLIGLEFIRKSQLVQPVGPLVVLLPLAGGYSRVLNAA

CQRLARAGVVLVTAAGNFRDDACLYSPASAPEVITVGATNAQDQPVTLGT

LGTNFGRCVDLFAPGEDIIGASSYCSTCFVSQSGTSQAAAHVAGIAAMML

SAEPELTLAELRQRLIHFSAKDVINEAWFPEDQRVLTPNLVAALPPSTHG

AGWQLFCRTVWSAHSGPTRMATAVARCAPDEELLSCSSFSRSGKRRGERM

EAQGGKLVCRAHNAFGGEGVYAIARCCLLPQANCSVHTAPPAEASMGTRV

HCHQQGHVLTGCSSHWEVEDLGTHKPPVLRPRGQPNQCVGHREASIHASC

CHAPGLECKVKEHGIPAPQEQVTVACEEGWTLTGCSALPGTSHVLGAYAV

DNTCVVRSRDVSTTGSTSEGAVTAVAICCRSRHLAQASQELQ*HHHHHH*

Note: Underlined sequence is a signal peptide, and italic part is His6-tag.
PCSK9 protein inserted with biotin receiving peptide BP15 and His tag: PCSK9-BP15-His6, as a detection reagent, biotin can be labeled to the BP15 peptide position during expression, avoiding the biotin labeling in vitro and consequently avoiding possible conformational changes.

SEQ ID NO: 5
MGTVSSRRSWWPLPLLLLLLLLLGPAGARAQEDEDGDYEELVLALRSEED

GLAEAPEHGTTATFHRCAKDPWRLPGTYVVVLKEETHLSQSERTARRLQA

QAARRGYLTKILHVFHGLLPGFLVKMSGDLLELALKLPHVDYIEEDSSVF

AQSIPWNLERITPPRYRADEYQPPDGGSLVEVYLLDTSIQSDHREIEGRV

MVTDFENVPEEDGTRFHRQASKCDSHGTHLAGVVSGRDAGVAKGASMRSL

RVLNCQGKGTVSGTLIGLEFIRKSQLVQPVGPLVVLLPLAGGYSRVLNAA

CQRLARAGVVLVTAAGNFRDDACLYSPASAPEVITVGATNAQDQPVTLGT

LGTNFGRCVDLFAPGEDIIGASSDCSTCFVSQSGTSQAAAHVAGIAAMML

SAEPELTLAELRQRLIHFSAKDVINEAWFPEDQRVLTPNLVAALPPSTHG

AGWQLFCRTVWSAHSGPTRMATAVARCAPDEELLSCSSFSRSGKRRGERM

EAQGGKLVCRAHNAFGGEGVYAIARCCLLPQANCSVHTAPPAEASMGTRV

HCHQQGHVLTGCSSHWEVEDLGTHKPPVLRPRGQPNQCVGHREASIHASC

CHAPGLECKVKEHGIPAPQEQVTVACEEGWTLTGCSALPGTSHVLGAYAV

DNTCVVRSRDVSTTGSTSEGAVTAVAICCRSRHLAQASQELQGSTSGSGL

NDIFEAQKIEWHE*HHHHHH*

NOTE: Underlined sequence is a signal peptide, double underlined sequence is the biotin receiving peptide, and italic part is the His6-tag.
PCSK9 D374Y mutant protein inserted with biotin receiving peptide BP15 and His tag: PCSK9-D374Y-BP15-His6, as a detection protein:

SEQ ID NO: 6
MGTVSSRRSWWPLPLLLLLLLLLGPAGARAQEDEDGDYEELVLALRSEED

GLAEAPEHGTTATFHRCAKDPWRLPGTYVVVLKEETHLSQSERTARRLQA

-continued

QAARRGYLTKILHVFHGLLPGFLVKMSGDLLELALKLPHVDYIEEDSSVF

AQSIPWNLERITPPRYRADEYQPPDDGGSLVEVYLLDTSIQSDHREIEGRV

MVTDFENVPEEDGTRFHRQASKCDSHGTHLAGVVSGRDAGVAKGASMRSL

RVLNCQGKGTVSGTLIGLEFIRKSQLVQPVGPLVVLLPLAGGYSRVLNAA

CQRLARAGVVLVTAAGNFRDDACLYSPASAPEVITVGATNAQDQPVTLGT

LGTNFGRCVDLFAPGEDIIGASSYCSTCFVSQSGTSQAAAHVAGIAAMML

SAEPELTLAELRQRLIHFSAKDVINEAWFPEDQRVLTPNLVAALPPSTHG

AGWQLFCRTVWSAHSGPTRMATAVARCAPDEELLSCSSFSRSGKRRGERM

EAQGGKLVCRAHNAFGGEGVYAIARCCLLPQANCSVHTAPPAEASMGTRV

HCHQQGHVLTGCSSHWEVEDLGTHKPPVLRPRGQPNQCVGHREASIHASC

CHAPGLECKVKEHGIPAPQEQVTVACEEGWTLTGCSALPGTSHVLGAYAV

DNTCVVRSRDVSTTGSTSEGAVTAVAICCRSRHLAQASQELQ<u>GSTSGSGL</u>

<u>NDIFEAQKIEWHE</u>*HHHHHH*

NOTE: Underlined sequence is a signal peptide, double underlined sequence is the biotin receiving peptide, and italic part is the His6-tag.
PCSK9 receptor protein LDLR extracellular domain with Flag tag and His tag: LDLR-ECD-Flag-His6 as a detection reagent;

SEQ ID NO: 7
<u>MGPWGWKLRWTVALLLAAAGTAVG</u>DRCERNEFQCQDGKCISYKWVCDGSA

ECQDGSDESQETCLSVTCKSGDFSCGGRVNRCIPQFWRCDGQVDCDNGSD

EQGCPPKTCSQDEFRCHDGKCISRQFVCDSDRDCLDGSDEASCPVLTCGP

ASFQCNSSTCIPQLWACDNDPDCEDGSDEWPQRCRGLYVFQGDSSPCSAF

EFHCLSGECIHSSWRCDGGPDCKDKSDEENCAVATCRPDEFQCSDGNCIH

GSRQCDREYDCKDMSDEVGCVNVTLCEGPNKFKCHSGECITLDKVCNMAR

DCRDWSDEPIKECGTNECLDNNGGCSHVCNDLKIGYECLCPDGFQLVAQR

RCEDIDECQDPDTCSQLCVNLEGGYKCQCEEGFQLDPHTKACKAVGSIAY

LFFTNRHEVRKMTLDRSEYTSLIPNLRNVVALDTEVASNRIYWSDLSQRM

ICSTQLDRAHGVSSYDTVISRDIQAPDGLAVDWIHSNIYWTDSVLGTVSV

ADTKGVKRKTLFRENGSKPRAIVVDPVHGFMYWTDWGTPAKIKKGGLNGV

DIYSLVTENIQWPNGITLDLLSGRLYWVDSKLHSISSIDVNGGNRKTILE

DEKRLAHPFSLAVFEDKVFWTDIINEAIFSANRLTGSDVNLLAENLLSPE

DMVLFHNLTQPRGVNWCERTTLSNGGCQYLCLPAPQINPHSPKFTCACPD

GMLLARDMRSCLTEAEAAVATQETSTVRLKVSSTAVRTQHTTTRPVPDTS

RLPGATPGLTTVEIVTMSHQALGDVAGRGNEKKPSSVR<u>DYKDDDDK</u>*HHHH*

*HH*

NOTE: Underlined sequence is a signal peptide, double underlined sequence is the Flag tag, and italic part is the His6-tag.
LCDR-Fc, a fusion protein of truncated LDLR extracellular domain with hIgG1 Fc (with PCSK9 binding activity): LDLR-sECD-Fc (hIgG1) as a detection reagent;

SEQ ID NO: 8
<u>MEFGLSWLFLVAILKGVQC</u>GTNECLDNNGGCSHVCNDLKIGYECLCPDGF

QLVAQRRCEDIDECQDPDTCSQLCVNLEGGYKCQCEEGFQLDPHTKACK*E*

*PKSSDKTHTCPPCPAPELLGGPSVFLFPPKPKDTLMISRTPEVTCVVVDV*

*SHEDPEVKFNWYVDGVEVHNAKTKPREEQYNSTYRVVSVLTVLHQDWLNG*

*KEYKCKVSNKALPAPIEKTISKAKGQPREPQVYTLPPSRDELTKNQVSLT*

*CLVKGFYPSDIAVEWESNGQPENNYKTTPPVLDSDGSFFLYSKLTVDKSR*

*WQQGNVFSCSVMHEALHNHYTQKSLSLSPGK*

NOTE: Underlined sequence is a signal peptide, double underlined sequence is the truncated LDLR extracellular domain with PCSK9 binding activity (LDLR-sECD), and italic part is the hIgG1-Fc.
A fusion protein of more truncated LDLR extracellular domain with hIgG1 Fc (with PCSK9 binding activity): LDLR-ssECD-Fc (hIgG1) as a detection reagent;

SEQ ID NO: 9
<u>MEFGLSWLFLVAILKGVQC</u>GTNECLDNNGGCSHVCNDLKIGYECLCPDGF

QLVAQRRCEDIDE*PKSSDKTHTCPPCPAPELLGGPSVFLFPPKPKDTLMI*

*SRTPEVTCVVVDVSHEDPEVKFNWYVDGVEVHNAKTKPREEQYNSTYRVV*

*SVLTVLHQDWLNGKEYKCKVSNKALPAPIEKTISKAKGQPREPQVYTLPP*

*SRDELTKNQVSLTCLVKGFYPSDIAVEWESNGQPENNYKTTPPVLDSDGS*

*FFLYSKLTVDKSRWQQGNVFSCSVMHEALHNHYTQKSLSLSPGK*

NOTE: Underlined sequence is a signal peptide, double underlined sequence is the more truncated LDLR extracellular domain with PCSK9 binding activity (LDLR-ssECD), and italic part is the hIgG1-Fc.

Example 2. Purified Recombinant Protein of PCSK9 and LDLR Related Recombinant Protein, and Purification of Hybridoma Antibody and Recombinant Antibody 1. Purification Steps of Recombinant Proteins with His-Tag:

The cell expression supernatant samples were centrifuged by high-speed centrifugation and impurities were removed. The buffer solution was exchanged by PBS and imidazole was added to the final concentration of 5 mM. The nickel column was balanced with PBS solution containing 5 mM imidazole, and washed with 2-5 column volumes. The supernatant sample after buffer exchange was loaded onto the IMAC column. The column was washed with PBS solution containing 5 mM imidazole, until the readout at $A_{280}$ was reduced to the baseline. Then, the chromatographic column was washed with PBS+10 mM imidazole to remove nonspecific binding proteins and efflux was collected. The target protein was eluted with PBS solution containing 300 mM imidazole and the elution peak was collected. The collected elution was concentrated and further purified by gel chromatography (GE) Superdex 200 and the mobile phase was PBS. The multimer peak was removed and the elution peaks were collected. The obtained proteins were identified by electrophoresis, peptide mapping and LC-MS. PCSK9-His6 (SEQ ID NO:1), PCSK9-PADRE-His6 (SEQ ID NO: 2), PCSK9-TEV-His6 (SEQ ID NO: 3), PCSK9-D374Y-His6 (SEQ ID NO: 4), PCSK9-BP15-His6 (SEQ ID NO: 5), and PCSK9-D374Y-BP15-His6 (SEQ ID NO: 6)

were obtained and were used as the immunogens or detection reagents of the invention. PCSK9-TEV-His6 was purified and cleaved by the TEV enzyme, and an IMAC column was used to remove TEV enzyme, incompletely cleaved PCSK9-TEV-His6 or C-terminal domain fragments with a His-tag. The IMAC effluent was concentrated and M-terminal PCSK9 domain fragment only was remained, and was used as an immunogen for immunizing mice.

2. Purification Steps of Recombinant Protein of LDLR-ECD-Flag-His6 (SEQ ID NO: 7) with His Tag and Flag Tag:

Samples were centrifuged by high-speed centrifugation and impurities were removed, and then the samples were concentrated to a proper volume. A Flag Affinity Column was equilibrated with 0.5×PBS and washed with 2-5 column volumes. After the impurity was removed, the cell expression supernatant samples were loaded onto the column. The column was washed with 0.5×PBS, until the readout at A280 was reduced to the baseline. The column was washed with PBS containing 0.3M NaCl, and proteins were washed and collected. Target proteins were eluted with 0.1M acetic acid (pH3.5-4.0) and collected, and then pH value was adjusted to neutral. The collected elution was concentrated and further purified by gel chromatography (GE) Superdex 200 and the mobile phase was PBS. The multimer peak was removed and the elution peaks were collected. The obtained proteins were identified by electrophoresis, peptide mapping and LC-MS. LDLR-ECD-Flag-His6 (SEQ ID NO: 7) with FLAG/His6 tags were obtained and were used for performance tests of the antibody of the present invention.

3. Purification Steps of Fusion Protein of LDLR Fc:

The cell expression supernatant samples were centrifuged by high-speed centrifugation and impurities were removed, and then the samples were concentrated to a proper volume and loaded onto a Protein A column. The column was washed with PBS until the readout at A280 was reduced to the baseline. Target proteins were eluted with 100 mM sodium acetate, pH 3.0 and then neutralized with 1M Tris-HCl. The eluted samples were properly concentrated and were further purified by gel chromatography (GE) Superdex 200 pre-equilibrated with PBS. The peaks without multimer were collected. This method was used to purify LDLR-sECD-Fc (hIgG1) (SEQ ID NO: 8) and LDLR-ssECD-Fc (hIgG1) (SEQ ID NO: 9). Both can be used for performance tests of the PCSK9 antibody.

Example 3. Preparation of Anti-Human PCSK9 Hybridoma Monoclonal Antibodies

1. Immunization

The anti-human PCSK9 monoclonal antibody was produced by immunizing mice. Experimental SJL white mice, female, 6 weeks old (Beijing Weitong Lihua Experimental Animal Technology Co., Ltd., animal production license number: SCXK (Beijing) 2012-0001). Feeding environment: SPF level. After the mice were purchased, the animals were kept in the laboratory for 1 week, 12/12 hours light/dark cycle, temperature 20-25° C., humidity 40-60%. The mice that had been adapted to the environment were immunized according to following two schemes, with 6-10 mice per group. The immunogens were human PCSK9-His6 (SEQ ID NO: 1) with His tag, PCSK9-PADRE-His6 (SEQ ID NO: 2), and N-PCSK9 (SEQ ID NO: 3).

Scheme A: emulsifying with Freund's adjuvant (sigma Lot Num: F5881/F5506): first immunization with Complete Freund's adjuvant (CFA), booster immunization with Incomplete Freund's adjuvant (IFA). The ratio of antigen to adjuvant was 1:1, 100 μg/mouse (for first immunization), 50 μg/mouse (for booster immunization). On day 0, mice were intraperitoneally (IP) injected with 100 μg/mouse of emulsified antigens, after first immunization, once every two weeks, total for 6-8 weeks.

Scheme B: Mice were cross immunized with Titermax (sigma Lot Num: T2684) and Alum (Thremo Lot Num: 77161). The ratio of antigen to adjuvant (titermax) was 1:1, and the ratio of antigen to adjuvant (Alum) was 3:1, 10-20 μg/mouse (for first immunization), 5 μg/mouse (for booster immunization). On day 0, mice were intraperitoneally (IP) injected with 20/10 μg/mouse of emulsified antigens, and once a week after first immunization, Titermax and Alum were alternately used, totally for 6-11 weeks. Four weeks after immunization, back or intraperitoneal injection with antigen was selected according to the swelling conditions on the back and abdomen.

2. Cell Fusion

Mice with high antibody titer in serum (See Tests 1 and 2, in combination with ELISA for PCSK9) and the titer tending to platform were chosen for splenocyte fusion. 72 hours before fusion, the chosen mice were immunized with PCSK9-His6, 10 μg/mouse via intraperitoneal injection. The spleen lymphocyte and myeloma cell Sp2/0 (ATCC® CRL-8287™) were fused to obtain hybridoma cells by an optimized fusion procedure mediated with PEG The fused hybridoma cells were re-suspended with HAT complete medium (RPMI-1640 medium containing 20% FBS, 1×HAT and 1×OPI), and then added into 96-well cell culture plate ($1\times10^5$/150 μl/well) and incubated at 37° C. and 5% $CO_2$. On day 5 after fusion, HAT complete medium was added at 50 μl/well, incubated at 37° C. and 5% $CO_2$. On day 7 to day 8 after fusion, based on cell growth density, the whole medium was exchanged to HT complete medium (RPMI-1640 medium containing 20% FBS, 1×HT and 1×OPI), 200 μl/well, and incubated at 37° C. and 5% $CO_2$.

3. Screening of Hybridoma Cells

On day 10 to day 11 after fusion, based on cell growth density, ELISA tests for PCSK9 or PCSK9-Y binding were performed (See tests 1 and 2). Positive cells in the binding ELISA test were used for testing the blockage of PCSK9 or PCSK9-Y binding to LDLR in the blocking ELISA test (See Tests 3 and 4). The medium in the positive well was exchanged and the cells were expanded to a 24-well plate based on cell density. The cell strains transferred into the 24-well plate were preserved and first sub-cloned after retest. The positive cells after the first sub-clone screening (See Tests 1 and 2) were preserved, and were subjected for the second sub-clone. The positive cells after the second sub-clone (See Tests 1 and 2) were preserved and analyzed for protein expression. Hybridoma cells capable of blocking the binding of PCSK9 or PCSK9-Y to LDLR were obtained after multiple times of fusion.

The hybridoma clone mAb-001 was obtained by screening according to the blocking assay and the binding assay. The antibody was further prepared by serum-free cell culturing. The antibodies were purified according to the exemplified purification steps, and were used in detection.

The mouse variable region sequence of the hybridoma clone mAb-001 was as follows:

> mAb-001 VH

SEQ ID NO: 10

QVHLQQSGAELAKPGASVKLSCKASGYTFN<u>DYWMH</u>WVKERPGQGLEWIG<u>Y</u>

<u>INPSSGFTKYHQNFKDKATLTADKSSSTAYMQLSSLTYDDSAVYYCARQY</u>

<u>DYDEDWYFDV</u>WGTGTTVTVSS

> mAb-001VL

SEQ ID NO: 11

*DIVMSQSPSSLAVSAGEKVTMSC*<u>KSSQSLLNSRTRKNFLA</u>*WYQQKPGQSP*

*KLLIY*<u>WASTRES</u>*GVPDRFTGRGSGTDFTLTISSVQAEDLAVYYC*<u>KQSFNL</u>

<u>FT</u>*FGSGTKLEIK*

Note: The order is FR1-CDR1-FR2-CDR2-FR3-CDR3-FR4, italic part is the FR sequence, and the underlined is CDR sequence.

TABLE 1

Heavy chain and light chain CDR region sequence

|  |  | Heavy Chain |  | Light Chain |
|---|---|---|---|---|
| mAb-001 | HCDR1 | DYWMH SEQ ID NO: 12 | LCDR1 | KSSQSLLNSRTRKNFLA SEQ ID NO: 15 |
|  | HCDR2 | YINPSSGFTKYHQNFKD SEQ ID NO: 13 | LCDR2 | WASTRES SEQ ID NO: 16 |
|  | HCDR3 | QYDYDEDWYFDV SEQ ID NO: 14 | LCDR3 | KQSFNLFT SEQ ID NO: 17 |

Example 4. Humanization of Anti-Human PCSK9 Hybridoma Monoclonal Antibody

1. Selection of Humanized Frame for Hybridoma Clone mAb-001

By comparing IMGT human antibody heavy and light chain variable region germline gene database and MOE software, the heavy and light chain variable region genes with high homology with mAb-001 were selected as templates. The CDRs of these two murine antibodies were respectively grafted into the corresponding human templates to form variable region sequences with the order of FR1-CDR1-FR2-CDR2-FR3-CDR3-FR4. Amino acid residues were numbered and annotated according to the Kabat numbering system.

The humanized light chain templates of mouse antibody mAb-001 are IGKV1-39*01 and hjk2.1, and the humanized heavy chain templates are IGHV1-2*02 and hjh2. The variable region sequence of humanized antibody h001-1 after humanization is showed as follows:

> h001-1 VH

SEQ ID NO: 18

*QVQLVQSGAEVKKPGASVKVSCKASGYTFT*<u>DYWMH</u>*WVRQAPGQGLEWMG*<u>Y</u>

<u>INPSSGFTKYHQNFKD</u>*RVTMTRDTSISTAYMELSRLRSDDTAVYYCAR*<u>QY</u>

<u>DYDEDWYFDV</u>*WGQGTTVTVSS*

> h001-1 VL

SEQ ID NO: 24

*DIQMTQSPSSLSASVGDRVTITC*<u>KSSQSLLNSRTRKNFLA</u>*WYQQKPGKAP*

*KLLIY*<u>WASTRES</u>*GVPSRFSGSGSGTDFTLTISSLQPEDFATYYC*<u>KQSFNL</u>

<u>FT</u>*FGQGTKLEIK*

Note: The order is FR1-CDR1-FR2-CDR2-FR3-CDR3-FR4, the italic is FR sequence, and the underlined is CDR sequence.

2. Template selection and back mutation design for hybridoma clone mAb-001 are shown in Table 2. The humanized sequence combination after back mutation of hybridoma is shown in Table 2.

TABLE 2

Template selection and back mutation design

| VH |  | SEQ ID NO | VL |  | SEQ ID NO |
|---|---|---|---|---|---|
| h001_VH.1 | Graft | 18 | h001_VL.1 | Graft | 24 |
| h001_VH.1A | T30N | 19 | h001_VL.1A | S66D | 25 |
| h001_VH.1B | R87T | 20 | h001_VL.1B | T5S, S66D | 26 |
| h001_VH.1C | T30N, R87T | 21 | h001_VL.1C | T5S, S66D, Q3V, A49S | 27 |
| h001_VH.1D | T30N, R87T, R72A, T74K | 22 |  |  |  |
| h001_VH.1E | T30N, R87T, R72A, T74K, M48I, V68A, M70L, R38K, R67K | 23 |  |  |  |

Notes:
For example, S66D means S on position 66 according to Kabat numbering system was back-mutated to D.

Graft represents that the mouse antibody CDRs were grafted into human FR region sequences.

The specific sequences of the mutant variable regions are shown in Table 3:

TABLE 3

| SEQ ID NO | Sequence |
|---|---|
| 19 | *QVQLVQSGAEVKKPGASVKVSCKASGYTFN*<u>DYWMH</u>*WVRQAPGQGLEWMG*<u>YINPSSGF</u> <u>TKYHQNFKD</u>*RVTMTRDTSISTAYMELSRLRSDDTAVYYCAR*<u>QYDYDEDWYFDV</u>*WGQGT TVTVSS* |

TABLE 3-continued

| SEQ ID NO | Sequence |
|---|---|
| 20 | QVQLVQSGAEVKKPGASVKVSCKASGYTFTDYWMHWVRQAPGQGLEWMGYINPSSGFT KYHQNFKDRVTMTRDTSISTAYMELSRLTSDDTAVYYCARQYDYDEDWYFDVWGQGTTV TVSS |
| 21 | QVQLVQSGAEVKKPGASVKVSCKASGYTFNDYWMHWVRQAPGQGLEWMGYINPSSGF TKYHQNFKDRVTMTRDTSISTAYMELSRLTSDDTAVYYCARQYDYDEDWYFDVWGQGTT VTVSS |
| 22 | QVQLVQSGAEVKKPGASVKVSCKASGYTFNDYWMHWVRQAPGQGLEWMGYINPSSGF TKYHQNFKDRVTMTADKSISTAYMELSRLTSDDTAVYYCARQYDYDEDWYFDVWGQGT TVTVSS |
| 23 | QVQLVQSGAEVKKPGASVKVSCKASGYTFNDYWMHWVKQAPGQGLEWIGYINPSSGFT KYHQNFKDKATLTADKSISTAYMELSRLTSDDTAVYYCARQYDYDEDWYFDVWGQGTTV TVSS |
| 25 | DIQMTQSPSSLSASVGDRVTITCKSSQSLLNSRTRKNFLAWYQQKPGKAPKLLIYWAST RESGVPDRFSGSGSGTDFTLTISSLQPEDFATYYCKQSFNLFTFGQGTKLEIK |
| 26 | DIQMSQSPSSLSASVGDRVTITCKSSQSLLNSRTRKNFLAWYQQKPGKAPKLLIYWAST RESGVPDRFSGSGSGTDFTLTISSLQPEDFATYYCKQSFNLFTFGQGTKLEIK |
| 27 | DIVMSQSPSSLSASVGDRVTITCKSSQSLLNSRTRKNFLAWYQQKPGKSPKLLIYWASTR ESGVPDRFSGSGSGTDFTLTISSLQPEDFATYYCKQSFNLFTFGQGTKLEIK |

Note:
Underlined parts are the CDR regions.

TABLE 4

Humanized sequence combination of mouse antibody mAb-001

|  | h001_VL.1 | h001_VL.1A | h001_VL.1B | h001_VL.1C |
|---|---|---|---|---|
| h001_VH.1 | h001-1 | h001-2 | h001-3 | h001-4 |
| h001_VH.1A | h001-5 | h001-6 | h001-7 | h001-8 |
| h001_VH.1B | h001-9 | h001-10 | h001-11 | h001-12 |
| h001_VH.1C | h001-13 | h001-14 | h001-15 | h001-16 |
| h001_VH.1D | h001-17 | h001-18 | h001-19 | h001-20 |
| h001_VH.1E | h001-21 | h001-22 | h001-23 | h001-24 |

Note:
The table indicates the humanized antibody variable regions obtained by combining various sequences and their mutant sequences. For example, as illustrated by h001-1, the variable region of humanized antibody h001-1 consists of light chain h001_VL.1 and heavy chain h001_VL.1 The others are combined in a similar way.

3. The above humanized sequences were combined to form an antibody, in which the heavy chain constant region is from human IgG1, the light chain constant region is from human kappa chain. The corresponding humanized antibody was obtained and analyzed for binding to PCSK9 by the ELISA method (See Test 1), and danalyzed for binding to PCSK9-Y by the ELISA method (See Test 2). The positive cells for binding detected in the above ELISA method were further detected for the blockage of PCSK9/LDLR binding in the blocking ELISA test (See Test 4), and were further detected for the blockage of PCSK9-Y/LDLR binding in the blocking ELISA test (See Test 3), the results are shown in Tables 5-8.

The results show that the PCSK9 antibodies obtained in the invention have high binding activity with PCSK9 and PCSK9-Y, also, the antibodies can effectively block the binding of PCSK9/PCSK9-Y to LDLR.

Example 5. Construction and Expression of Anti-Human PCSK9 Humanized Antibodies in IgG1 and IgG1-YTE Formats Thereof The method of construction and expression of anti-human PCSK9 humanized antibodies was shown as follows:

1. Primer design: Multiple primers were designed by using online software DNAWorks (v3.2.2, World Wide Web at helixweb.nih.gov/dnaworks) to synthesize VH/VK containing gene fragments necessary for recombination: 5'-30 bp Signal peptide+VH/VK+30 bp CH1/CL-3'. The principle of primer design: if the target gene 2 is different from the target gene 1 in 2 amino acids, a further primer located at the mutation site was designed, as shown in FIG. 1.

2. Fragment splicing: according to the Manuals for TakaRa Primer STAR GXL DNA polymerase, two-step PCR amplification was performed with the multiple primers designed above and VH/VK containing gene fragments necessary for recombination was obtained.

3. Construction of expression vector pHr (with signal peptide and constant region gene (CH1-FC/CL) fragment) and restriction enzyme digestion.

Figure 2:
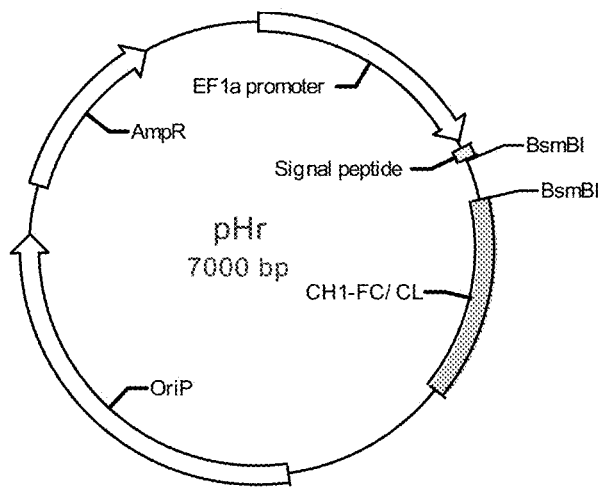
FIG. 2: A schematic for constructing vectors of the antibodies according to the present invention.

Expression vector pHr (with signal peptide and constant region gene (CH1-FC/CL) fragment) were designed and constructed by using some special restriction enzymes, such as BsmBI, which recognizes sequences different from the enzyme digestion site, as shown in FIG. 2. BsmBI was used to cut the vector, and the gel was cut and recovered for use.

4. Construction of the recombinant expression vector VH-CH1-FC-pHr/VK-CL-pHr.

VH/VK containing the gene fragments necessary for recombination and the recovered expression vector pHr digested with BsmBI enzyme (with the signal peptide and the constant region gene (CH1-FC/CL) fragment) were added into the DH5 alpha competent cells at the ratio of 3:1, incubated in ice bath at 0° C. for 30 min, heat shocked for 90 seconds at 42° C., and added with 5-times volume of LB medium, incubated at 37° C. for 45 min, plated on LB-Amp plate, and cultured at 37° C. overnight. A single clone was picked up and sequenced.

The antibody of this invention can be constructed from, but not restricted to, the above method. For example, an antibody containing h001-4 or a variant thereof can be designed and obtained as the following: 1) h001-4-WT: an IgG1 format of h001-4, i.e., a combination of the humanized variable region h001-4, with the heavy chain constant region from human IgG1 and the light chain constant region from human kappa chain; or 2) h001-4-YTE: an h001-4-IgG1-YTE format, i.e., a combination of the humanized variable region h001-4, with the heavy chain constant region of a mutant human IgG1 (YTE mutation) and the light chain constant region from human kappa chain. The mutant human IgG1 can also be other forms of mutant. The obtained antibodies and mutant antibodies were analyzed for affinity by BIAcore detection (Test 6), and the results are shown in Table 9.

The Sequences of Constructed and Expressed Anti-human PCSK9 Humanized Antibodies (IgG1 and IgG1-YTE Formats thereof) are shown as follows:

H001-4 IgG1 format, heavy chain constant region is from human IgG1 and light chain constant region is from human kappa light chain:

```
Heavy chain amino acid sequence (with Human IgG1):
                                              SEQ ID NO: 28
QVQLVQSGAEVKKPGASVKVSCKASGYTFTDYWMHWVRQAPGQGLEWMGY

INPSSGFTKYHQNFKDRVTMTRDTSISTAYMELSRLRSDDTAVYYCARQY

DYDEDWYFDVWGQGTTVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPG

K

Heavy chain DNA sequence:
                                              SEQ ID NO: 29
ATGGAGTTTGGGCTGAGCTGGCTTTTTCTTGTCGCGATTCTTAAGGGTGT

CCAGTGCCAGGTGCAGCTGGTGCAGAGCGGCGCTGAGGTGAAGAAGCCCG

GAGCGAGCGTAAAGGTGAGCTGCAAGGCCAGCGGATACACCTTCACCGAC

TACTGGATGCACTGGGTGAGGCAGGCCCCAGGACAGGGCCTGGAGTGGAT

GGGCTACATCAACCCCAGCAGCGGCTTTACCAAGTATCACCAGAACTTCA

AAGACAGGGTGACCATGACCAGGGACACCAGCATCAGCACCGCCTACATG

GAGCTGAGCAGGCTGAGGAGCGACGACACCGCCGTGTACTACTGCGCCAG

GCAATACGACTACGACGAGGACTGGTACTTCGACGTGTGGGGCCAAGGAA

CCACCGTGACTGTGAGCAGCGCTTCGACCAAGGGCCCATCGGTCTTCCCC

CTGGCACCCTCCTCCAAGAGCACCTCTGGGGGCACAGCGGCCCTGGGCTG

CCTGGTCAAGGACTACTTCCCCGAACCGGTGACGGTGTCGTGGAACTCAG

GCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGG

CACCCAGACCTACATCTGCAACGTGAATCACAAGCCCAGCAACACCAAGG

TGGACAAGAAAGTTGAGCCCAAATCTTGTGACAAAACTCACACATGCCCA

CCGTGCCCAGCACCTGAACTCCTGGGGGGACCGTCAGTCTTCCTCTTCCC

CCCAAAACCCAAGGACACCCTCATGATCTCCCGGACCCCTGAGGTCACAT

GCGTGGTGGTGGACGTGAGCCACGAAGACCCTGAGGTCAAGTTCAACTGG

TACGTGGACGGCGTGGAGGTGCATAATGCCAAGACAAAGCCGCGGGAGGA

GCAGTACAACAGCACGTACCGTGTGGTCAGCGTCCTCACCGTCCTGCACC

AGGACTGGCTGAATGGCAAGGAGTACAAGTGCAAGGTCTCCAACAAAGCC

CTCCCAGCCCCCATCGAGAAAACCATCTCCAAAGCCAAAGGGCAGCCCCG

AGAACCACAGGTGTACACCCTGCCCCCATCCCGGGATGAGCTGACCAAGA

ACCAGGTCAGCCTGACCTGCCTGGTCAAAGGCTTCTATCCCAGCGACATC

GCCGTGGAGTGGGAGAGCAATGGGCAGCCGGAGAACAACTACAAGACCAC

GCCTCCCGTGCTGGACTCCGACGGCTCCTTCTTCCTCTACAGCAAGCTCA

CCGTGGACAAGAGCAGGTGGCAGCAGGGGAACGTCTTCTCATGCTCCGTG

ATGCATGAGGCTCTGCACAACCACTACACGCAGAAGAGCCTCTCCCTGTC

TCCGGGTAAATGA h001-4-kappa
Light chain amino acid sequence:
                                              SEQ ID NO: 30
DIVMSQSPSSLSASVGDRVTITCKSSQSLLNSRTRKNFLAWYQQKPGKSP

KLLIYWASTRESGVPDRFSGSGSGTDFTLTISSLQPEDFATYYCKQSFNL

FTFGQGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

Light chain DNA sequence:
                                              SEQ ID NO: 31
ATGGACATGCGCGTGCCCGCCCAGCTGCTGGGCCTGCTGCTGCTGTGGTT

CCCCGGCTCGCGATGCGACATCGTGATGTCTCAGAGCCCATCTAGCCTGA

GCGCCAGCGTGGGCGACAGGGTAACCATCACCTGCAAGAGCAGCCAAAGC

CTGCTGAACAGCAGGACCCGCAAGAACTTCCTGGCTTGGTATCAGCAGAA

GCCCGGCAAGTCTCCCAAGTTGCTGATCTACTGGGCCAGCACCAGGGAGA

GCGGCGTGCCCGACAGGTTCAGCGGCTCCGGCAGCGGCACCGACTTCACC

CTGACCATCTCTAGTCTGCAGCCCGAGGACTTCGCCACCTACTACTGCAA

GCAGAGCTTCAATCTGTTCACCTTCGGCCAGGGCACCAAGCTGGAGATCA

AGCGTACGGTGGCTGCACCATCTGTCTTCATCTTCCCGCCATCTGATGAG

CAGTTGAAATCTGGAACTGCCTCTGTTGTGTGCCTGCTGAATAACTTCTA

TCCCAGAGAGGCCAAAGTACAGTGGAAGGTGGATAACGCCCTCCAATCGG
```

-continued

GTAACTCCCAGGAGAGTGTCACAGAGCAGGACAGCAAGGACAGCACCTAC

AGCCTCAGCAGCACCCTGACGCTGAGCAAAGCAGACTACGAGAAACACAA

AGTCTACGCCTGCGAAGTCACCCATCAGGGCCTGAGCTCGCCCGTCACAA

AGAGCTTCAACAGGGGAGAGTGTTGA h001-4-IgG1-YTE (Light chain is
h001-4-kappa: SEQ ID NO: 30)
Heavy chain amino acid sequence: IgG1-YTE
SEQ ID NO: 32
QVQLVQSGAEVKKPGASVKVSCKASGYTFTDYWMHWVRQAPGQGLEWMGY

INPSSGFTKYHQNFKDRVTMTRDTSISTAYMELSRLRSDDTAVYYCARQY

DYDEDWYFDVWGQGTTVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPPK

PKDTLYITREPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPG

K

Heavy chain DNA sequence:
SEQ ID NO: 33
ATGGAGTTTGGGCTGAGCTGGCTTTTTCTTGTCGCGATTCTTAAGGGTGT

CCAGTGCCAGGTGCAGCTGGTGCAGAGCGGCGCTGAGGTGAAGAAGCCCG

GAGCGAGCGTAAAGGTGAGCTGCAAGGCCAGCGGATACACCTTCACCGAC

TACTGGATGCACTGGGTGAGGCAGGCCCCAGGACAGGGCCTGGAGTGGAT

GGGCTACATCAACCCCAGCAGCGGCTTTACCAAGTATCACCAGAACTTCA

AAGACAGGGTGACCATGACCAGGGACACCAGCATCAGCACCGCCTACATG

GAGCTGAGCAGGCTGAGGAGCGACGACACCGCCGTGTACTACTGCGCCAG

GCAATACGACTACGACGAGGACTGGTACTTCGACGTGTGGGGCCAAGGAA

CCACCGTGACTGTGAGCAGCGCTTCGACCAAGGGCCCATCGGTCTTCCCC

CTGGCACCCTCCTCCAAGAGCACCTCTGGGGGCACAGCGGCCCTGGGCTG

CCTGGTCAAGGACTACTTCCCCGAACCGGTGACGGTGTCGTGGAACTCAG

GCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGG

CACCCAGACCTACATCTGCAACGTGAATCACAAGCCCAGCAACACCAAGG

TGGACAAGAAAGTTGAGCCCAAATCTTGTGACAAAACTCACACATGCCCA

CCGTGCCCAGCACCTGAACTCCTGGGGGGACCGTCAGTCTTCCTCTTCCC

CCCAAAACCCAAGGACACCCTCTACATCACCCGGGAGCCTGAGGTCACAT

GCGTGGTGGTGGACGTGAGCCACGAAGACCCTGAGGTCAAGTTCAACTGG

TACGTGGACGGCGTGGAGGTGCATAATGCCAAGACAAAGCCGCGGGAGGA

GCAGTACAACAGCACGTACCGTGTGGTCAGCGTCCTCACCGTCCTGCACC

AGGACTGGCTGAATGGCAAGGAGTACAAGTGCAAGGTCTCCAACAAAGCC

CTCCCAGCCCCCATCGAGAAAACCATCTCCAAAGCCAAAGGGCAGCCCCG

AGAACCACAGGTGTACACCCTGCCCCCATCCCGGGATGAGCTGACCAAGA

ACCAGGTCAGCCTGACCTGCCTGGTCAAAGGCTTCTATCCCAGCGACATC

GCCGTGGAGTGGGAGAGCAATGGGCAGCCGGAGAACAACTACAAGACCAC

GCCTCCCGTGCTGGACTCCGACGGCTCCTTCTTCCTCTACAGCAAGCTCA

CCGTGGACAAGAGCAGGTGGCAGCAGGGGAACGTCTTCTCATGCTCCGTG

ATGCATGAGGCTCTGCACAACCACTACACGCAGAAGAGCCTCTCCCTGTC

TCCGGGTAAATGA
Note:
Underlined part is signal peptide DNA sequence.

The performance and benefits of the present invention are verified by biochemical tests as indicated below.

Test 1. ELISA Test for Binding of PCSK9 Antibodies to Wildtype PCSK9 Protein

The binding ability of anti-PCSK9 antibodies of the present invention to PCSK9 was detected by measuring the amount of antibodies binding to wild-type PCSK9 protein (WT PCSK9, SEQ ID NO: 5) fixed on the ELISA plate.

Streptavidin (sigma, CAT # S4762) was diluted to 2 µg/ml with PBS and coated into 96-well ELISA plate, at 4° C. overnight. The plate was washed and then blocked with Tris buffer (including 0.9 mM CaCl2, 0.05% Tween 20 and 5% skim milk) at 37° C. for 2 hours. Then the plate was washed again and 100 µl/well of the biotin-labeled PCSK9, produced in-house, (bio-WT-PCSK9, diluted with Tris buffer containing 0.9 mM CaCl2, 0.05% Tween 20 and 1% skim milk), was added and incubated at 37° C. for 1 hour. After the wash step, different concentrations of diluted PCSK9 antibody samples was added to the plate and incubated at 37° C. for 1 hour. Then the plate was washed again and HRP-goat-anti-human (H+L) antibody (Jackson ImmunoResearch, CAT #109-035-088) was added and incubated at 37° C. for 1 hour. Then the plate was washed again and tetramethylbenzidine solution was added for development. Finally, the stop solution was added and the OD450 value was measured on the Microplate reader, and then EC50 was calculated.

The results of ELISA test for the binding ability of chimeric antibodies and back-mutated antibodies of the present invention to human PCSK9 protein are shown in table 5.

TABLE 5

| Binding Assay of PCSK9 antibodies of the present invention to PCSK9 | |
|---|---|
| Clone No. | EC50 (µg/ml) |
| h001-1 | 0.0084 |
| h001-2 | 0.0123 |
| h001-3 | 0.0113 |
| h001-4 | 0.012 |
| h001-5 | 0.0141 |
| h001-6 | 0.01 |
| h001-7 | 0.012 |
| h001-8 | 0.009 |
| h001-9 | 0.0136 |
| h001-10 | 0.0176 |
| h001-11 | 0.0129 |
| h001-12 | 0.0103 |
| h001-13 | 0.0071 |
| h001-14 | 0.0084 |
| h001-15 | 0.011 |
| h001-16 | 0.0082 |
| h001-17 | 0.0114 |
| h001-18 | 0.0147 |
| h001-19 | 0.0139 |
| h001-20 | 0.0126 |

TABLE 5-continued

Binding Assay of PCSK9 antibodies of the present invention to PCSK9

| Clone No. | EC50 (µg/ml) |
| --- | --- |
| h001-21 | 0.0145 |
| h001-22 | 0.0123 |
| h001-23 | 0.0118 |
| h001-24 | 0.0092 |
| Ch-001 | 0.0084 |

The data showed that the humanized antibodies of the present invention have higher binding activity to human PCSK9 protein.

Test 2 ELISA Test for Binding of PCSK9 Antibodies to PCSK9-Y

The binding ability of anti-PCSK9 antibodies of the present invention to PCSK9-Y was detected by measuring the amount of antibodies binding to PCSK9-Y (mutant PCSK9, SEQ ID NO: 6) fixed on the ELISA plate.

Streptavidin (sigma, CAT #54762) was diluted to 2 µg/ml with PBS and coated into 96-well ELISA plate at 4° C. overnight. The plate was washed and then blocked with Tris buffer (including 0.9 mM $CaCl_2$, 0.05% Tween 20 and 5% skim milk) at 37° C. for 2 hours. Then the plate was washed again and 100 µl/well of the biotin-labeled PCSK9-Y, produced in-house, (bio-PCSK9-Y, diluted with Tris buffer containing 0.9 mM $CaCl_2$, 0.05% Tween 20 and 1% skim milk) was added and incubated at 37° C. for 1 hour. After the wash step, different concentrations of diluted PCSK9 antibody samples were added to the plate and incubated at 37° C. for 1 hour. Then the plate was washed again and HRP-goat-anti-human (H+L) antibody (Jackson ImmunoResearch, CAT #109-035-088) was added and incubated at 37° C. for 1 hour. Then the plate was washed again and tetramethylbenzidine solution was added for development. Finally, the stop solution was added and the OD450 value was measured on the Microplate reader, and then EC50 was calculated.

The results of ELISA test for the binding ability of chimeric antibodies and back-mutated antibodies of the present invention to mutant PCSK9 are shown in table 6.

TABLE 6

Binding Assay of PCSK9 antibodies of the present invention to PCSK9-Y

| Clone No. | EC50 (µg/ml) |
| --- | --- |
| h001-1 | 0.0132 |
| h001-2 | 0.0157 |
| h001-3 | 0.0152 |
| h001-4 | 0.0179 |
| h001-5 | 0.0152 |
| h001-6 | 0.0144 |
| h001-7 | 0.0137 |
| h001-8 | 0.0165 |
| h001-9 | 0.0194 |
| h001-10 | 0.0209 |
| h001-11 | 0.0170 |

TABLE 6-continued

Binding Assay of PCSK9 antibodies of the present invention to PCSK9-Y

| Clone No. | EC50 (µg/ml) |
| --- | --- |
| h001-12 | 0.0124 |
| h001-13 | 0.0096 |
| h001-14 | 0.0112 |
| h001-15 | 0.0178 |
| h001-16 | 0.0111 |
| h001-17 | 0.0161 |
| h001-18 | 0.0191 |
| h001-19 | 0.0204 |
| h001-20 | 0.0170 |
| h001-21 | 0.0119 |
| h001-22 | 0.0111 |
| h001-23 | 0.0125 |
| h001-24 | 0.0170 |
| Ch-001 | 0.0132 |

The data showed that the humanized antibodies of the present invention have higher binding activity to PCSK9-Y.

Test 3 Anti-PCSK9 Antibodies Block the Binding of LDLR-FC/PCSK9-Y

The blocking abilities of anti-PCSK9 antibodies to the binding of LDLR-FC (SEQ ID NO: 8) to PCSK9-Y (mutant PCSK9, SEQ ID NO: 6) were detected by measuring the amount of PCSK9-Y binding to LDLR in the presence of the antibodies.

LDLR-FC was diluted to 2 µg/ml with phosphate buffer and coated in the 96-well ELISA plate (Costar, CAT #3590), then incubated at 4° C. overnight. The plate was washed and then blocked with Tris buffer (including 0.9 mM $CaCl_2$, 0.05% Tween 20 and 5% skim milk) at 37° C. for 2 hours. Then the plate was washed again and 100 µl/well of the mixture of biotin-labeled PCSK9-Y (bio-PCSK9-Y, diluted to final concentration of 1 g/ml with Tris buffer containing 0.9 mM $CaCl_2$, 0.05% Tween 20 and 1% skim milk) and antibody samples (diluted with Tris buffer containing 0.9 mM $CaCl_2$, 0.05% Tween 20 and 1% skim milk) were added and incubated at 37° C. for 1 hour. Then the plate was washed again and horseradish peroxidase-streptavidin (sigma, CAT # S2438) was added and incubated at 37° C. for 1 hour. Then the plate was washed and tetramethylbenzidine solution was added for development. Finally, the stop solution was added and the OD450 value was measured on the Microplate reader, then IC50 was calculated.

The results of blocking test for the blocking effects of the chimeric antibodies and back-mutated antibodies of the present invention on the binding of LDLR-FC/PCSK9-Y are shown in table 7.

TABLE 7

Blocking effects of PCSK9 antibodies on the binding of PCSK9-Y to LDLR

| Clone No. | IC50 (µg/ml) |
| --- | --- |
| h001-1 | 0.5658 |
| h001-2 | 0.4553 |
| h001-3 | 0.4749 |
| h001-4 | 0.5302 |
| h001-5 | 0.4677 |
| h001-6 | 0.4374 |
| h001-7 | 0.5150 |

TABLE 7-continued

Blocking effects of PCSK9 antibodies
on the binding of PCSK9-Y to LDLR

| Clone No. | IC50 (µg/ml) |
|---|---|
| h001-8 | 0.4145 |
| h001-9 | 0.5203 |
| h001-10 | 0.5142 |
| Ch-001 | 0.3915 |

The data showed that the PCSK9 antibodies of the present invention can efficiently block the binding of PCSK9-Y to LDLR.

The blocking effects of PCSK9 antibodies of the present invention on the binding of other formats of LDLR-FC (produced in-house, sequence is shown in SEQ ID NO: 7 or SEQ ID NO: 9) to PCSK9-Y (SEQ ID NO: 5) were also tested with the above methods. The results show that the PCSK9 antibodies of the present invention can efficiently block the binding of PCSK9-Y to the truncated LDLRs.

Test 4 Anti-PCSK9 Antibodies Block the Binding of LDLR-FC/PCSK9

The blocking abilities of PCSK9 antibodies of the present invention to the binding of LDLR-FC (produced in-house, sequence is shown in SEQ ID NO: 8) to PCSK9 (SEQ ID NO: 5) were detected by measuring the amount of PCSK9 binding to LDLR in the presence of the antibodies.

LDLR-FC was diluted to 5 µg/ml with phosphate buffer and coated in the 96-well ELISA plate, then incubated at 4° C. overnight. The plate was washed and then blocked with Tris buffer (including 0.9 mM $CaCl_2$, 0.05% Tween 20 and 5% skim milk) at 37° C. for 2 hours. Then the plate was washed again and 100 µl/well of the mixture of biotin-labeled PCSK9 (bio-WT-PCSK9, diluted to the final concentration of 2 µg/ml with Tris buffer containing 0.9 mM $CaCl_2$, 0.05% Tween 20 and 1% skim milk) and antibody samples (diluted with Tris buffer containing 0.9 mM $CaCl_2$, 0.05% Tween 20 and 1% skim milk) were added and incubated at 37° C. for 1 hour. Then the plate was washed again and horseradish peroxidase-streptavidin (Sigma, CAT #52438) was added and incubated at 37° C. for 1 hour. Then the plate was washed and tetramethylbenzidine solution was added for development. Finally, the stop solution was added and the OD450 was measured on the Microplate reader, then IC50 was calculated.

The results of blocking test for the blocking effects of the chimeric antibodies and back-mutated antibodies of the present invention on the binding of LDLR-FC/PCSK9 are shown in table 8.

TABLE 8

Blocking effects of PCSK9 antibodies
on the binding of PCSK9 and LDLR

| Clone No. | IC50 (µg/ml) |
|---|---|
| h001-1 | 0.4997 |
| h001-2 | 0.6750 |
| h001-3 | 0.7021 |
| h001-4 | 0.7597 |
| h001-5 | 4.322 |
| h001-6 | 0.6620 |
| h001-7 | 0.6521 |
| h001-8 | 0.7738 |
| h001-9 | 0.9230 |
| h001-10 | 0.8290 |
| Ch-001 | 0.8363 |

The data showed that the PCSK9 antibodies of the present invention can efficiently block the binding of PCSK9 to LDLR.

The blocking effects of PCSK9 antibodies of the present invention on the binding of other formats of LDLR-FC (produced in-house, sequence is shown in SEQ ID NO: 7 or SEQ ID NO: 9) and PCSK9 (SEQ ID NO: 5) were also tested with the above methods. The results show that the PCSK9 antibodies of the present invention can efficiently block the binding of PCSK9 to the truncated LDLRs.

Test 5 Effects of PCSK9 Antibodies on LDL Uptake

Figure 3:
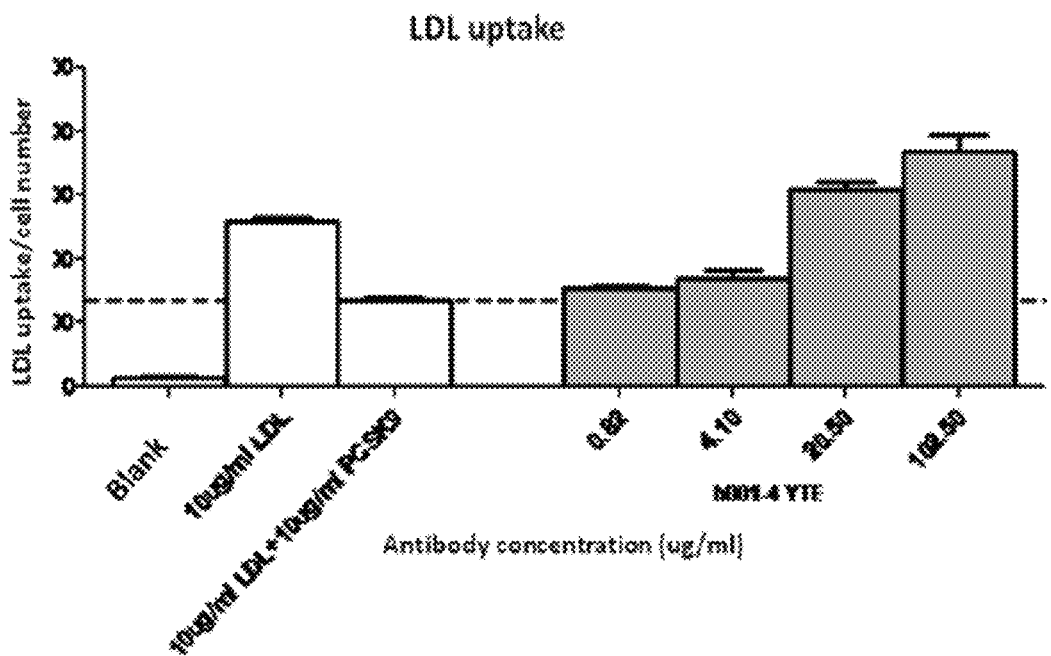
FIG. 3: Change in LDL uptake by HepG2 cells under different concentrations of h001-4-YTE PCSK9 antibody. The results show that the PCSK9 antibody can promote LDL uptake by HepG2 cells.
Figure 4:
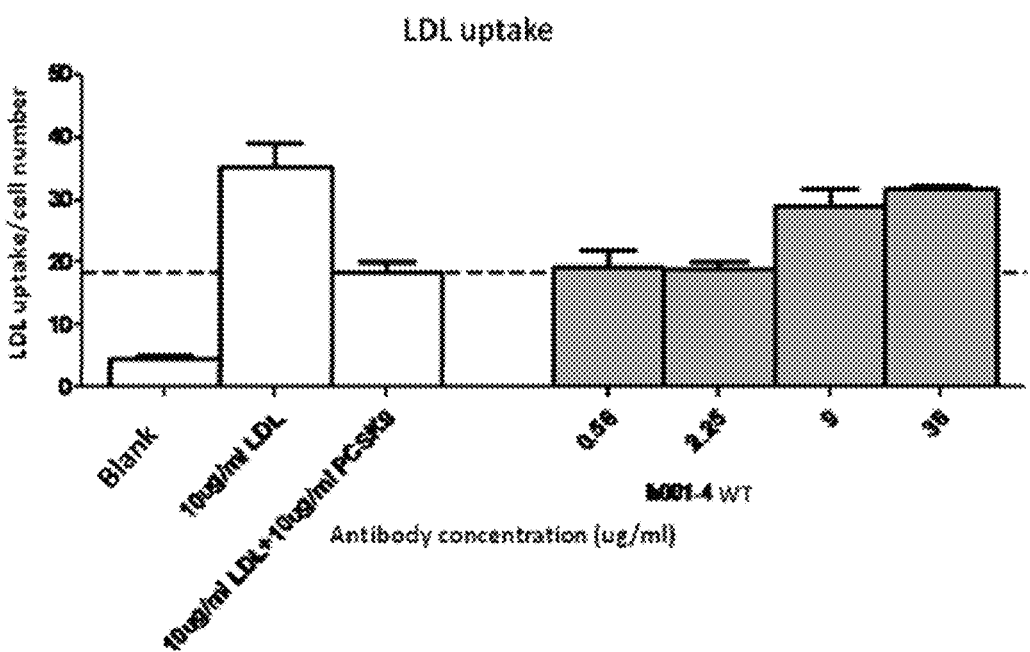
FIG. 4: Change in LDL uptake by HepG2 cells under different concentrations of h001-4-WT PCSK9 antibody. The results show that the PCSK9 antibody can promote LDL uptake by HepG2 cells.

HepG2 cells (Chinese Academy of Sciences cell bank, # CAT, TCHu72) were cultured in DMEM medium (Hyclone, # CAT SH30243.01B) (containing 10% FBS, Gibco, # CAT 10099-141). When cells covered 80-90% of the plate, the cells were digested, suspended, and counted, $1.5*10^4$ cells/well were plated in 96-well plate. 24 hours later, the medium was replaced with DMEM and 10% serum without lipoprotein (Millipore, CAT # LP4). 48 hours later, the plate was washed twice with PBS buffer, then a mixture, which was pre-incubated at 4° C. for 1 hour, containing PCSK9 (SEQ ID NO: 1, at a final concentration of 10 µg/ml) antibody samples (diluted to various concentrations with the medium), and BODIPY-®LDL at a final concentration of 10 µg/ml (Invitrogen, CAT # L3483) was added to the plate. After being incubated at 37° C. for 6 hours, the plate was washed twice with PBS buffer. The fluorescence value was read on Microplate reader (EX485 nm/EM535 nm), then 50 µl/well of CellTiter-Glo® Cell Activity Luminescence Detection Reagent (Promega, G7571) was added, and the chemiluminescence value was read. LDL uptake results are shown in FIGS. 3 and 4, which indicated that PCSK9 antibodies of the present invention can promote the LDL uptake by HepG2 cells.

Test 6 BIAcore Assay for PCSK9 Antibody Affinity

According to the method described in the Human Fab Capture Kit (Cat. #28-9583-25, GE), the human Fab capture molecule was covalently linked to the CM5 biochip (Cat. # BR-1000-12, GE) so that the antibodies to be tested were affinity captured. Then, human PCSK9 antigen (human PCSK9 with His tag: PCSK9-His6, SEQ ID NO: 1) flowed through the surface of the biochip, and the reaction signal was detected in real time using a Biacore instrument to obtain the association and dissociation curves. Finally, the affinity values were obtained by fitting and are shown at table 9 below. After each cycle of dissociation was finished in the experiment, the biochip was washed and regenerated with regeneration solution in Human Fab Capture kit (GE).

TABLE 9

Affinity of PCSK9 Antibody

| Stationary phase | Mobile phase | Affinity KD(M) |
|---|---|---|
| h001-4-WT | huPCSK9 | 2.88E−10 |
| h001-4-YTE |  | 4.91E−10 |

The result demonstrated that the PCSK9 antibodies of present invention have strong affinity to PCSK9 antigen.

The same method was also used to detect the affinities of PCSK9 antibodies of the present invention to PCSK9-Y (SEQ ID NO: 4), and the results demonstrated that the PCSK9 antibodies of the present invention have strong affinity to PCSK9-Y antigen.

Test 7 Pharmacodynamic Test of PCSK9 Antibodies In Vivo

A human PCSK9-overexpressing mouse model was constructed and the mice were injected with PCSK9 antibody via the tail vein. The effect of the PCSK9 antibodies according to the present invention on reducing LDL-c level in vivo in human PCSK9-overexpressing mice was evaluated. Human IgG (human immunoglobulin purified from the mixed normal human serum by traditional affinity chromatography, such as Protein A) was used as blank control.

C57Bl/6 mice (purchased from Shanghai Sippr-BK Laboratory Animal Co., Ltd.) were adapted for 5 days in the laboratory environment, and injected with $4 \times 10^{11}$ v·g of AAV-PCSK9 virus (Benyuan Zhengyang Gene Technology Co., Ltd.) via tail vein. After the virus injection, the mice were fasted overnight. On the next day, then blood was taken from the eyelid and LDL-c was detected with HDL and LDL/VLDL Cholesterol Quantification Kit (purchased from BioVision, catalog number # K613-100). Mice were randomly divided into groups (6 mice/group (n=6)) according to the concentration of LDL-c and were administered with antibodies via tail vein injection. Human IgG and h001-4-WT antibody, produced in-house, were administered at a dose of 10 mg/kg (human IgG and h001-4-WT antibody were both prepared in PBS at a concentration of 1 mg/ml). The mice were fasted for six hours before blood sampling. 24 h, 48 h, 72 h and 96 h after administration, blood was taken from the eyelids, kept at 37° C. for 1 hour, centrifuged at 3500 rpm for 10 minutes, and the serum was stored at −80° C.

After the last serum collection, all the frozen serum were tested on the same day. The concentration of LDL-c in the serum was detected with HDL and LDL/VLDL Cholesterol Quantification Kit in accordance with kit instructions.

Figure 5:
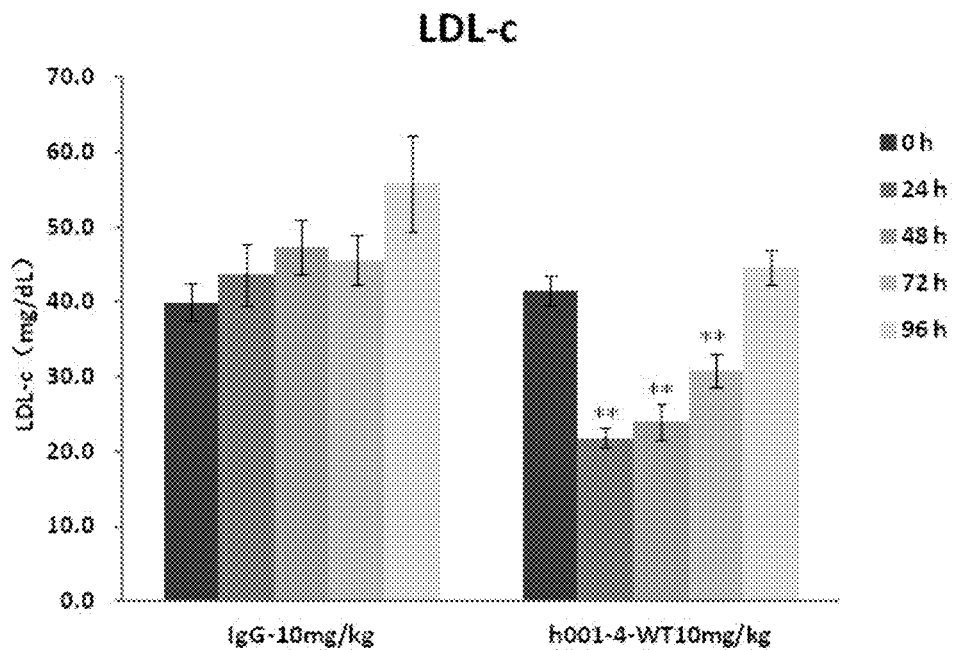
FIG. 5: Changes of serum concentrations of LDL-c over time in mice after injection with h001-4-WT PCSK9 antibody (*: $p<0.05$, vs IgG **: $p<0.01$, vs IgG). The results show that the PCSK9 antibody can reduce the serum concentration of LDL-c in human PCSK9-overexpressing mice.
Figure 6:
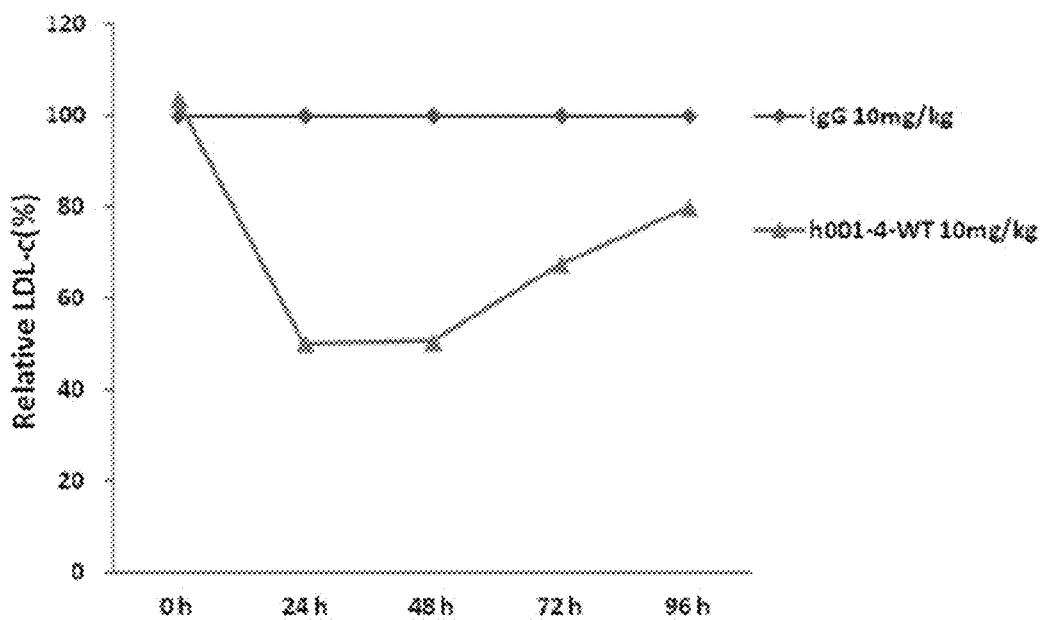
FIG. 6: Changes of serum concentration of LDL-c in mice injected with h001-4-WT PCSK9 antibody relative to the IgG group. The results show that compared to the IgG group, PCSK9 antibody can reduce the serum concentration of LDL-c in human PCSK9-overexpressing mice.

As shown in FIG. 5, the results show that the concentration of LDL-c in the serum of normal mouse is about 12 mg/dl. After the injection of AAV8-PCSK9 virus, the concentration of LDL-c in the serum was averaged at 40 mg/dl. Mice were divided into groups and antibodies were administered. 24 h after administration, the concentration of LDL-c in the h001-4-WT group was decreased by 50% compared to the IgG group; 48 h after administration, the concentration of LDL-c in the h001-4-WT group was decreased by 49%; 72 h after administration, the concentration of LDL-c in the h001-4-WT group was decreased by 32%; 96 h after administration, the concentration of LDL-c in the h001-4-WT group was decreased by 20%, as shown in Table 10 and FIG. 6.

In summary, h001-4-WT was able to reduce the concentration of LDL-c in the serum of human PCSK9-overexpressing mice, and the effect lasts for 72 hours.

Test 8 Competitive Experiment

In the competitive ELISA experiment, the plate was coated with one antibody overnight. Then biotin-PCSK9-his and a competitive antibody at a concentration of 50 times higher than the coating antibody were added together. The coating antibody will compete with the competitive antibody to bind to an antigen. The antigen signal at the plate was then tested. The results show that, h001-4 and 21B12 (U.S. Pat. No. 8,030,457B2) per se can compete to bind to the antigen, however, there is no clear competition binding between the two antibodies, suggesting antigen epitopes of the two antibodies are different.

| IR (%) | h001-4 | 21B12 |
|---|---|---|
| h001-4 | 95.97 | 0.42 |
| 21B12 | 3.86 | 97.78 |

Test 9 Pharmacodynamic and Pharmacokinetic Test in Cynomolgus Macaques In Vivo

In order to investigate the in vivo effect and metabolism of the antibodies of the present invention, h001-4-WT and h001-4-YTE were administered in vivo to Cynomolgus macaques, respectively. The administration dosage was 3 mg/kg by intravenous administration, and each group comprises 3 male Cynomolgus macaques. The intravenous injection was at a speed of about 2-4 mL/min. Blood samples were taken at different time points for detection of the concentration of lipoprotein, especially of low-density lipoprotein (LDL), and the concentration of the antibodies in serum. The time points for detection of lipoprotein were pre-dosing and 1, 4, 8, 12, 16, 20, 24, and 28 days post-dosing. The blood collection time points for PK were pre-dosing and 15 minutes, 30 minutes, 1 hour, 3 hours, 8 hours, 12 hours, 24 hours, 48 hours, 72 hours, 96 hours, 120 hours, 144 hours, 168 hours, 336 hours, 504 hours, and 672 hours post-dosing.

Figure 7:
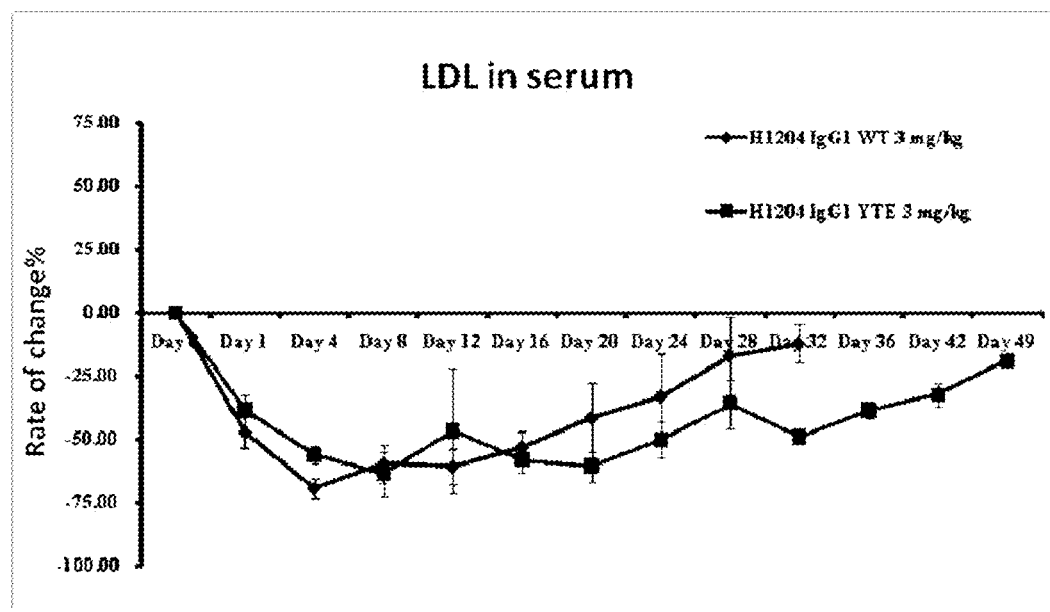
FIG. 7: The pharmacodynamic and pharmacokinetic test of the antibody according to the present invention in vivo in Cynomolgus macaques. The figure shows h001-4-WT and h001-4-YTE can both significantly reduce the content of LDL in Cynomolgus macaques, and the duration of the decrease induced by h001-4-YTE is superior to that induced by h001-4-WT.

The results showed that (FIG. 7) both h001-4-WT and h001-4-YTE can significantly reduce the content of LDL in Cynomolgus macaques, and the duration of the decrease induced by h001-4-YTE was superior to that induced by h001-4-WT.

The contents of h001-4-WT and h001-4-YTE in the serum samples taken for PK were determined by ELISA. The method was described in Test 1 and the results show that the half-life of h001-4-WT in Cynomolgus macaques is 4 days, while the half-life of h001-4-YTE in Cynomolgus macaques is 7.3 days. YTE has a significantly increased half-life in vivo than WT.

TABLE 10

Changes in serum concentration of LDL-c in mice

| | LDL-c (mg/dl) | | | | | % IgG | | | | |
|---|---|---|---|---|---|---|---|---|---|---|
| | 0 h | 24 h | 48 h | 72 h | 96 h | 0 h | 24 h | 48 h | 72 h | 96 h |
| IgG-10 mg/kg | 40.0 ± 2.42 | 43.6 ± 4.16 | 47.4 ± 3.61 | 45.6 ± 3.35 | 55.8 ± 6.54 | 100 | 100 | 100 | 100 | 100 |
| h001-4-WT-10 mg/kg | 41.4 ± 2.01 | 21.9 ± 1.21 | 24.0 ± 2.49 | 30.8 ± 2.17 | 44.6 ± 2.37 | 104 | 50 | 51 | 68 | 80 |

The invention claimed is:

1. A PCSK9 antibody or the antigen-binding fragment thereof, wherein the antibody comprises a HCDR1, a HCDR2, and a HCDR3 as shown in SEQ ID NO: 12, SEQ ID NO: 13 and SEQ ID NO: 14, respectively; and
   a LCDR1, a LCDR2, and a LCDR3 as shown in SEQ ID NO: 15, SEQ ID NO: 16 and SEQ ID NO: 17, respectively.

2. The PCSK9 antibody or the antigen-binding fragment thereof according to claim 1, wherein the PCSK9 antibody or antigen-binding fragment thereof is a murine antibody or fragment thereof.

3. The PCSK9 antibody or the antigen-binding fragment thereof according to claim 1, wherein the PCSK9 antibody light chain variable region further comprises light chain FR regions selected from a murine κ chain or murine λ chain; wherein the PCSK9 antibody heavy chain variable region further comprises heavy chain FR regions selected from a murine IgG1, a murine IgG2, or a murine IgG3.

4. The PCSK9 antibody or the antigen-binding fragment thereof according to claim 3, comprising the heavy chain variable region of SEQ ID NO: 10 and the light chain variable region of SEQ ID NO: 11.

5. The PCSK9 antibody or the antigen-binding fragment thereof according to claim 1, wherein the PCSK9 antibody light chain further comprises light chain constant regions selected from a murine κ chain or a murine λ chain; wherein the PCSK9 antibody heavy chain further comprises heavy chain constant regions selected from a murine IgG1, a murine IgG2, or a murine IgG3.

6. The PCSK9 antibody or the antigen-binding fragment thereof according to claim 1, wherein the PCSK9 antibody or antigen-binding fragment thereof is a chimeric antibody or fragment thereof.

7. The PCSK9 antibody or the antigen-binding fragment thereof according to claim 1, wherein the PCSK9 antibody or antigen-binding fragment thereof is a humanized antibody or fragment thereof.

8. The PCSK9 antibody or the antigen-binding fragment thereof according to claim 7, wherein the heavy chain FR sequence of the heavy chain variable region of the humanized antibody is selected from a combination sequence of human germline heavy chains IGHV1-2*02 and hjh2; wherein the humanized antibody comprises a FR1, a FR2, a FR3 of human germline heavy chain IGHV1-2*02 and a FR4 of hjh2.

9. The PCSK9 antibody or the antigen-binding fragment thereof according to claim 8, wherein the humanized antibody contains a heavy chain variable region of SEQ ID NO: 18 or a variant thereof; wherein the variant comprises 1-10 amino acid changes in SEQ ID NO: 18.

10. The PCSK9 antibody or the antigen-binding fragment thereof according to claim 9, wherein the variant of SEQ ID NO: 18 has 1-9 amino acid back-mutations in the FR regions, wherein the back-mutation is selected from the group consisting of T3ON, R87T, R72A, T74K, M48I, V68A, M7OL, R38K and R67K.

11. The PCSK9 antibody or the antigen-binding fragment thereof according to claim 8, wherein the humanized antibody contains a heavy chain variable region selected from the group consisting of SEQ ID NO:19, SEQ ID NO: 20, SEQ ID NO: 21, SEQ ID NO: 22, and SEQ ID NO: 23.

12. The PCSK9 antibody or the antigen-binding fragment thereof according to claim 7, wherein the light chain FR sequence of the light chain variable region of the humanized antibody is selected from a combination sequence of human germline light chains IGKV1-39*01 and hjk2.1; wherein the humanized antibody comprises a FR1, a FR2, a FR3 of human germline IGKV1-39*01 and a FR4 of hjk2.1.

13. The PCSK9 antibody or the antigen-binding fragment thereof according to claim 12, wherein the humanized antibody further comprises a light chain variable region as shown in SEQ ID NO: 24 or a variant thereof, wherein the variant comprises 1-10 amino acid changes in SEQ ID NO: 24.

14. The PCSK9 antibody or the antigen-binding fragment thereof according to claim 13, wherein the variant of SEQ ID NO: 24 has 1-4 amino acid back-mutations in the FR regions, wherein the back-mutation is selected from the group consisting of T5S, S66D, Q3V and A49S.

15. The PCSK9 antibody or the antigen-binding fragment thereof according to claim 12, wherein the humanized antibody comprises a light chain variable region selected from the group consisting of SEQ ID NO:25, SEQ ID NO: 26, and SEQ ID NO: 27.

16. The PCSK9 antibody or the antigen-binding fragment thereof according to claim 7, wherein the humanized antibody comprises a heavy chain variable region and/or a light chain variable region, wherein the heavy chain variable region is selected from the group consisting of SEQ ID NO: 19, SEQ ID NO: 20, SEQ ID NO: 21, SEQ ID NO: 22, and SEQ ID NO: 23, or the heavy chain variable region has at least 95% identity to a sequence selected from the group consisting of SEQ ID NO: 19, SEQ ID NO: 20, SEQ ID NO: 21, SEQ ID NO: 22, and SEQ ID NO: 23; wherein the light chain variable region is selected from the group consisting of SEQ ID NO: 25, SEQ ID NO: 26, and SEQ ID NO: 27, or the light chain variable region has at least 95% identity to a sequence selected from the group consisting of SEQ ID NO: 25, SEQ ID NO: 26, and SEQ ID NO: 27.

17. The PCSK9 antibody or the antigen-binding fragment thereof according to claim 7, wherein the PCSK9 antibody comprises a heavy chain variable region and a light chain variable region selected from the group consisting of:
   1) the heavy chain variable region sequence of SEQ ID NO: 18 and the light chain variable region sequence of SEQ ID NO: 25,
   2) the heavy chain variable region sequence of SEQ ID NO: 18 and the light chain variable region sequence of SEQ ID NO: 26,
   3) the heavy chain variable region sequence of SEQ ID NO: 18 and the light chain variable region sequence of SEQ ID NO: 27,
   4) the heavy chain variable region sequence of SEQ ID NO: 19 and the light chain variable region sequence of SEQ ID NO: 24,
   5) the heavy chain variable region sequence of SEQ ID NO: 19 and the light chain variable region sequence of SEQ ID NO: 25, 6) the heavy chain variable region sequence of SEQ ID NO: 19 and the light chain variable region sequence of SEQ ID NO: 26,
7) the heavy chain variable region sequence of SEQ ID NO: 19 and the light chain variable region sequence of SEQ ID NO: 27,
8) the heavy chain variable region sequence of SEQ ID NO: 20 and the light chain variable region sequence of SEQ ID NO: 24,
9) the heavy chain variable region sequence of SEQ ID NO: 20 and the light chain variable region sequence of SEQ ID NO: 25,
10) the heavy chain variable region sequence of SEQ ID NO: 20 and the light chain variable region sequence of SEQ ID NO: 26,
11) the heavy chain variable region sequence of SEQ ID NO: 20 and the light chain variable region sequence of SEQ ID NO: 27,
12) the heavy chain variable region sequence of SEQ ID NO: 21 and the light chain variable region sequence of SEQ ID NO: 24,
13) the heavy chain variable region sequence of SEQ ID NO: 21 and the light chain variable region sequence of SEQ ID NO: 25,
14) the heavy chain variable region sequence of SEQ ID NO: 21 and the light chain variable region sequence of SEQ ID NO: 26,
15) the heavy chain variable region sequence of SEQ ID NO: 21 and the light chain variable region sequence of SEQ ID NO: 27,
16) the heavy chain variable region sequence of SEQ ID NO: 22 and the light chain variable region sequence of SEQ ID NO: 24,
17) the heavy chain variable region sequence of SEQ ID NO: 22 and the light chain variable region sequence of SEQ ID NO: 25,
18) the heavy chain variable region sequence of SEQ ID NO: 22 and the light chain variable region sequence of SEQ ID NO: 26,
19) the heavy chain variable region sequence of SEQ ID NO: 22 and the light chain variable region sequence of SEQ ID NO: 27,
20) the heavy chain variable region sequence of SEQ ID NO: 23 and the light chain variable region sequence of SEQ ID NO: 24,
21) the heavy chain variable region sequence of SEQ ID NO: 23 and the light chain variable region sequence of SEQ ID NO: 25,
22) the heavy chain variable region sequence of SEQ ID NO: 23 and the light chain variable region sequence of SEQ ID NO: 26,
23) the heavy chain variable region sequence of SEQ ID NO: 23 and the light chain variable region sequence of SEQ ID NO: 27, and
24) the heavy chain variable region sequence of SEQ ID NO: 18 and the light chain variable region sequence of SEQ ID NO: 24.

18. The PCSK9 antibody or the antigen-binding fragment thereof according to claim 6, wherein the heavy chain further comprises a heavy chain constant region selected from a human IgG1, IgG2, IgG3, or IgG4;
wherein the PCSK9 antibody further comprises a light chain constant region selected from a human κ chain or a human λ chain.

19. The PCSK9 antibody or the antigen-binding fragment thereof according to claim 18, wherein the humanized antibody comprises a heavy chain and a light chain selected the group consisting of:
1) the heavy chain of SEQ ID NO: 28 and the light chain of SEQ ID NO: 30, and
2) the heavy chain of SEQ ID NO: 32 and the light chain of SEQ ID NO: 30.

20. A pharmaceutical composition, comprising a therapeutically effective amount of the PCSK9 antibody or the antigen-binging fragment according to claim 1 and one or more pharmaceutically acceptable carriers, diluents, or excipients.

21. A nucleic acid molecule, encoding the PCSK9 antibody or the antigen-binding fragment thereof according to claim 1.

22. An expression vector comprising the nucleic acid molecule according to claim 21.

23. An isolated host cell transformed with the expression vector according to claim 22, wherein the host cell is selected from the group consisting of a prokaryotic cell and a eukaryotic cell.

24. A method of treating a PCSK9-mediated disease or disorder in a subject in need thereof, comprising administering to the subject the pharmaceutical composition of claim 20, wherein the disease or disorder is selected from the group consisting of hypercholesterolemia, heart disease, metabolic syndrome, diabetes, coronary heart disease, strokes, cardiovascular disease, Alzheimer's disease and general Dyslipidemia.

* * * * *